US008815237B2

(12) United States Patent
Wittrup et al.

(10) Patent No.: US 8,815,237 B2
(45) Date of Patent: Aug. 26, 2014

(54) AGLYCOSYLATED IMMUNOGLOBULIN MUTANTS

(75) Inventors: K. Dane Wittrup, Chestnut Hill, MA (US); Jeffrey Ravetch, New York, NY (US); Stephen Lael Sazinsky, Brookline, MA (US)

(73) Assignees: Massachusetts Institute of Technology, Cambridge, MA (US); The Rockefeller University, New York, NY (US)

( * ) Notice: Subject to any disclaimer, the term of this patent is extended or adjusted under 35 U.S.C. 154(b) by 1025 days.

(21) Appl. No.: 12/746,411

(22) PCT Filed: Dec. 5, 2008

(86) PCT No.: PCT/US2008/085757
§ 371 (c)(1),
(2), (4) Date: Nov. 22, 2010

(87) PCT Pub. No.: WO2009/079242
PCT Pub. Date: Jun. 25, 2009

(65) Prior Publication Data
US 2011/0059075 A1      Mar. 10, 2011

Related U.S. Application Data

(60) Provisional application No. 60/992,644, filed on Dec. 5, 2007, provisional application No. 61/050,196, filed on May 2, 2008.

(51) Int. Cl.
*A61K 39/395* (2006.01)
(52) U.S. Cl.
USPC ..................................... 424/133.1; 530/387.1
(58) Field of Classification Search
None
See application file for complete search history.

(56) References Cited

U.S. PATENT DOCUMENTS 8,188,231 B2 * 5/2012 Lazar et al. ................ 530/387.1
2007/0048300 A1 3/2007 Taylor

OTHER PUBLICATIONS

Sayers et al. Journal of Biological Chemistry, vol. 279, No. 34, pp. 35320-35325, Aug. 2004.*
Arnold, J. N., et al., "The Impact of Glycosylation on the Biological Function and Structure of Human Immunoglobulins," *Ann. Rev. Immunol. Ann. Review*, 25(1): 21-50 (2007).
Basset, C., et al., "Glycosylation of Immunoglobulin A Influences Its Receptor Binding," *Scandinavian J. Immunol.*, 50(6): 572-579 (1999).
European Patent Application No. 08862572.8: European Search Report dated Jun. 6, 2012.
Leader, K. A., et al., "Functional interactions of aglycosylated monoclonal anti-D with Fc gamma RI+ and Fc gamma RIII+ cells," *Immunol.*, 72(4): 481-485 (1991).
Leatherbarrow, R.J., et al., "Effector functions of a monoclonal aglycosylated mouse IgG2a: binding and activation of complement component C1 and interaction with human monocyte Fc receptor," *Mol., Immunol.*, 22(4): 407-415 (1985).
Pound, J.D., et al., "Aglycosylated Chimeric Human IgG3 Can Trigger the Human Phagocyte Respiratory Burst," *Mol. Immunol.*, 30(3): 233-241 (1993).
Sarmay, G., et al., "Mapping and comparison of the interaction sites on the Fc region of IgG responsible for triggering antibody dependent cellular cytotoxicity (ADCC) through different types of human Fc gamma receptor," *Mol. Immunol.*, 29(5): 633-639 (1992).
Sayers, I., et al., "The Importance of Lys-352 of Human Immunoglobulin E in FcepsilonR11/CD23 Recognition," *J. Bio. Chem.*, 279 (34): 35320-35325 (2004).
Sazinsky, S.L, et al., "Aglycosylated immunoglobulin $G_1$ variants productively engage activating Fc receptors," *Proc. Nat. Acad. Sci.*, 105(51): 20167-20172 (2008).
Shields, R.L., et al., "High Resolution Mapping of the Binding Site on Human IgG1 for FCgammaRI, FcgammaRII, FCgammaRIII, and FcRn and Design of IgG1 Variants with Improved Binding to the FcgammaR," *J. Bio. Chem.*, 276(9): 6591-6604 (2001).

* cited by examiner

*Primary Examiner* — Laura B Goddard
*Assistant Examiner* — Meera Natarajan
(74) *Attorney, Agent, or Firm* — Hamilton, Brook, Smith & Reynolds, P.C.

(57) ABSTRACT

The present invention is based, in part, on our discovery of immunoglobulins (e.g., immunoglobulin G (IgG)) polypeptides (e.g., murine or human IgG, such as human IgG1) that are aglycosylated yet retain the ability to bind to an Fc receptor, such as an activating Fc receptor (e.g., FcγRIIA and/or FcγRIIIA).

19 Claims, 8 Drawing Sheets

FIGs. 7A and 7B
A
B
$^{234}$LLGGPS$^{239}$     lower hinge
$^{265}$DVSHED$^{270}$     B/C loop
$^{326}$KALPAPIEK$^{334}$     F/G loop
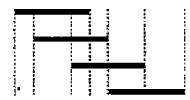

FIG. 13

Table 1: IgG CH2 domain mutants that retained Fc binding.

| designation | Amino acid position in C'/E loop | | | | | Amino acid position outside the C'/E loop | |
|---|---|---|---|---|---|---|---|
| | 296 | 297 | 298 | 299 | 300 | 290 | 326 |
| Wild-type | Y | N | S | T | Y | K | K |
| Double mutants: 298/299 | | | G | A | | | |
| | | | G | G | | | |
| Double mutants: 298/299 and outside the C'/E loop | | | G | A | | | E |
| | | | G | A | | E | E |
| | | | G | A | | N | E |
| Single mutants: 297 | | C | | | | | |
| | | D | | | | | |
| | | H | | | | | |
| Double mutants: 297/298 | | D | A | | | | |
| | | D | T | | | | |
| | | H | A | | | | |
| Single mutants: 298 | | | A, C, D, E, F, G, H, I, K, L, M, N, Q, R, T, V, W, Y | | | | |
| Single mutants:299 | | | | A | | | |
| | | | | H | | | |
| | | | | S | | | |
| Single mutants:299 and outside the C'/E loop | | | | A | | | |
| | | | | A | | | E |
| | | | | A | | | |
| | | | | A | | | E |
| | | | | A | | | E |
| Single mutants: 300 | | | | | D | | |
| | | | | | A | | |
| | | | | | G | | |
| | | | | | V | | |
| | | | | | T | | |
| | | | | | I | | |
| | | | | | W | | |

AGLYCOSYLATED IMMUNOGLOBULIN MUTANTS

CROSS-REFERENCE TO RELATED APPLICATION

This application is a U.S. national phase application in accordance with 35 U.S.C. §371, which claims priority from International Application No. PCT/US2008/085757, which was filed Dec. 5, 2008, which claims the benefit of the filing date of U.S. Provisional Application No. 60/992,644, which was filed on Dec. 5, 2007, and the benefit of the filing date of U.S. Provisional Application No. 61/050,196, which was filed on May 2, 2008. The contents of the earlier filed applications listed here are hereby incorporated by reference in their entirety.

FEDERALLY SPONSORED RESEARCH OR DEVELOPMENT

This invention was made with government support under Grant No. 5-R01-CA096504-05 awarded by the NIH. The government has certain rights in this invention.

INCORPORATION BY REFERENCE OF MATERIAL IN ASCII TEXT FILE

This application incorporates by reference the Sequence Listing contained in the following ASCII text file:
a) File name: 0050.2197-003 SUBSTITUTE SEQUENCE LISTING.txt; created Jul. 11, 2014, 25.5 KB in size.

TECHNICAL FIELD

This invention relates to mutant polypeptides, including mutant immunoglobulin polypeptides, and related therapeutics, methods of treatment, and methods of producing the polypeptides.

BACKGROUND

It is generally accepted that N-linked glycosylation in the IgG CH2 domain is required for functional engagement of activating FcγR receptors. For example, Jefferis et al., reported that "[o]ne of the most intriguing issues is that glycosylation of IgG-Fc is essential for the recognition by FcRs although the carbohydrate moieties are on the periphery of the FcRIII-Fc interface" (Jefferis at al., *J. Biol. Chem.* 276:45539, 2001). Similarly, other researchers have stated, "[g]lycosylation of IgG at the conserved asparagine residue at position 297, which is in the CH2 domain (immunoglobulin heavy-chain constant domain 2), is required to support the interaction between IgG and FcγRs, which is a prerequisite for ADCC80" (*Nat. Rev. Immunol.* 6:343, 2006).

The need for specific N-linked glycosylation necessitates the use of mammalian cell cultures for antibody production. However, the cost for antibodies manufactured in that way is considerable, and it is difficult and expensive to build sufficient capacity for the rising number of antibody drugs in development. Antibodies are among the most expensive of all drugs where the annual cost per patient can be 35,000 USD or more. The high cost reflects the fact that antibodies are now marketed for chronic conditions and of their relatively low potency results in the need for high cumulative doses. Consequently, expensive large-scale production capacity is currently required to fulfill market demand and produce tens to hundreds of kilograms of product per year. Use of bacterial fermentation to produce IgG would be economically beneficial. A process that routinely takes several months in mammalian systems can take as little as one month with *E. coli*. Fermentation capital costs for therapeutic proteins are also lower for bacterial production systems (*J. Immunol. Meth.* 263:133, 2002). Unfortunately, when wild type IgGs are produced in *E. coli*, they do not bind Fc receptors. *E. coli*-produced aglycosylated IgG1 failed to bind C1q and the FcγRI receptor, suggesting to prior investigators that the *E. coli*-derived IgG1 lacked effector functions (*J. Immunol. Meth.* 263:133, 2002).

Effector functions are a key component of efficacy for anti-cancer antibodies, one of the primary targets for antibody drug development. Antibody activity in vivo requires efficient interaction between the antibody and cellular Fc-receptors on innate immune effector cells, and it has been reported that the cytotoxic activity of antibodies in vivo is mainly determined by the co-engagement of activating and inhibitory FcRs (*Curr. Op. Immunol.* 19:239, 2007). In fact, in the absence of functional Fc/FcR interactions, several therapeutic antibodies were completely ineffective in mouse xenografted tumor models (*Nature Med.* 6:433, 2000).

SUMMARY

The present invention is based, in part, on our discovery of immunoglobulins (e.g., immunoglobulin G (IgG)) polypeptides (e.g., murine or human IgG, such as human IgG1) that are aglycosylated yet retain the ability to bind to an Fc receptor, such as an activating Fc receptor (e.g., FcγRIIA and/or FγRIIIA). We may use the term "immunoglobulin(s)" and "antibody" or "antibodies" interchangeably, and such polypeptides and portions and variants thereof (any of which we may refer to as a "polypeptide") are within the scope of the present invention.

In one embodiment, the present antibodies comprise a mutation in the Fc region that effectively eliminates antibody glycosylation (e.g., antibodies having one, two, three, or more mutant residues within one or more of the regions described below). The aglycosylated antibody exhibits substantial binding to an activating Fc receptor relative to the corresponding wild type antibody. For example, the aglycosylated antibody may exhibit at least or about 50%, 60%, 70%, 75%, 80%, 85%, 90%, 95%, 100% or more of the binding activity exhibited by the corresponding wild type antibody.

The aglycosylated antibody or an Fc region or other biologically active fragment or variant thereof can be derived from any antibody class (e.g., an immunoglobulin of the G class). As described further below, the antibody can also be a human or humanized antibody or a biologically active fragment or other variant thereof. As our compositions (i.e., the antibodies and other polypeptides described herein) are aglycosylated and bind to an activating Fc receptor in the manner described, a biologically active fragment or other variant thereof is a fragment or variant that exhibits similar or comparable (or even superior) Fc receptor binding activity.

The mutation can comprise a mutation within the C'/E loop of the CH2 domain (i.e., residues 297-299 numbered according to the EU index as in Kabat et al., 1991, infra). Any one, any two, or all three of residues 297-299 can be mutated, and the mutation can constitute the substitution of the wild type amino acid residue at a given position with another amino acid residue. For example, the present polypeptides may comprise a mutation at position 298 and/or 299 of the CH2 domain. The mutation at position 298 can be a substitution of the wild type residue with a glycine residue and/or the mutation at position 299 can be a substitution of the wild type residue with an alanine, glycine, or histidine residue. Alternatively, as is the case for any of the polypeptides described herein, the polypeptide (e.g., an aglycosylated antibody) can have mutations at only the positions specified.

In some embodiments, the aglycosylated antibody will have a mutation at position 297, which can be, for example, a substitution of the wild type residue with a cysteine, aspartic acid, or histidine residue.

As described, a polypeptide (e.g., an aglycosylated antibody) can have a mutation within the C'/E loop. Alternatively or in addition, the present polypeptides (e.g., the present aglycosylated antibodies) can have a mutation within the CH2 domain but outside the C'/E loop. For example, an aglycosylated antibody can include one or more mutations at one or more of positions 234-239, 265-270, 290 or 326-334. According to the Kabat numbering system, residues 234-239 constitute the lower hinge, residues 265-270 constitute the B/C loop, and residues 326 to 334 constitute the F/G loop.

In any instance, the activating Fc receptor can the activating receptor FcγRIIA or FcγRIIIA.

In more specific embodiments, the present polypeptides (e.g., aglycosylated antibodies, Fc regions, or Fc fusion polypeptides) can include one or more of the following mutations: E269D, D270E, N297D, N297H, S298A, S298G, S298T, T299A, T299G, T299H, K326E, K326I, A327E, A327Y, L328A, and L328G.

Also within the present invention are polypeptides (e.g., any of the antibody or antibody-related polypeptides described herein) that (a) comprise a mutation within the C'/E loop, (b) comprise a mutation within the F/G loop, (c) are not glycosylated, and (d) substantially retain or exceed the ability of the corresponding wild type antibody to bind FcγRIIIA. In this context the antibodies can include more than one mutation within the F/G loop. For example, the antibodies can include any or all of the mutations K326I, A327Y, and L328G or any or all of the mutations K326I, A327E, and L328A. These antibodies can further include a mutation in the C'/E loop.

In any instance, the polypeptide (e.g., an aglycosylated antibody) can specifically bind a cancer antigen or be useful as a cancer therapeutic.

An immunoglobulin that is aglycosylated or lacks glycosylation may be an immunoglobulin that is not glycosylated at all; that is not fully glycosylated; or that is atypically glycosylated (i.e., the glycosylation pattern for the mutant differs from the glycosylation pattern of the corresponding wild type immunoglobulin). The mutant IgG polypeptides can be expressed in prokaryotic (e.g., bacterial (e.g., *E. coli*)) or eukaryotic (e.g., yeast (e.g., *S. cerevisiae*) or mammalian) cells. Accordingly, the invention also features nucleic acids that encode the mutant immunoglobulins, expression vectors that include those nucleic acids, and cells that express the mutant immunoglobulins. The nucleic acids and expression vectors can include a leader sequence, which may be wild-type or mutant.

Also within the invention are methods of identifying an antibody that is an aglycosylated mutant that retains Fc receptor binding activity. The methods can be carried out by (a) displaying a library of randomly mutated Fc regions on the surface of a cell; and (b) identifying Fc regions that are aglycosylated but that bind to a soluble Fc receptor. For example, the Fc region can be the Fc region of a human IgG1 and the soluble Fc receptor can be represented by an FcγR/streptavidin tetramer. The cell can be a yeast cell, and displaying the library can comprise a secretion surface capture method.

The aglycosylated antibodies of the invention are useful therapeutic proteins and can specifically bind to antigens implicated in a wide range of diseases or disorders, e.g., cancer antigens. For example, the antibodies can specifically bind cancer antigens, antigens involved in neurological disorders, cardiovascular disorders or infectious agents.

Accordingly, the invention features physiologically acceptable compositions and concentrated stocks of aglycosylated immunoglobulins that can be formulated for administration to a patient diagnosed as having, for example, cancer. The IgG's can be partially or substantially purified. For example, the compositions can an include IgG polypeptide having one or more of the mutations described in Table 1 or they can include mixtures of the variants described in Table 1 (FIG. 13). The polypeptides of the invention can be formulated in any pharmaceutically acceptable medium. Carriers and stabilizing agents may be added to facilitate drug delivery and to insure shelf-life. For example, encapsulation of the polypeptides in a suitable delivery vehicle (e.g., polymeric microparticles or implantable devices) may increase the efficiency of delivery.

The availability of mutant immunoglobulins (e.g., human IgGs) that retain one or more (and up to all) FcR-mediated effector functions enables significantly less expensive microbial manufacture of therapeutic antibodies (e.g., anti-cancer antibodies). Their availability also provides for methods of isolating mutant antibodies with increased affinity for activating FcRs and decreased affinity for inhibitory FcRs.

BRIEF DESCRIPTION OF THE DRAWINGS

FIG. 2A shows the unique sequences of aglycosylated Fc variants isolated for FcγRIIA binding after two rounds of FACS. Displayed sequences represent the residues randomized in the saturation libraries, positions 296-300, with the wild-type sequence underlined. The numbers in parentheses denote the number of times a particular mutant was isolated; in some cases, identical protein sequences were isolated from multiple unique clones at the DNA level. Sequences of glycosylated variants enriched from the screen have been omitted. FIG. 2B shows the unique sequences within aglycosylated Fc variants isolated for FcγRIIA binding after a third round of FACS, using a more stringent screening strategy. FIG. 2C is a bar graph showing the results of binding of yeast-produced 4m5.3 hIgG1 variants to 10 nM FcγRIIA131R streptavidin-Alexa 647 tetramers. IgG from yeast culture supernatants was loaded onto fluorescein-conjugated yeast and median fluorescence intensity (MFI) of receptor labeling was measured by flow cytometry. All data represent the average of two trials.

FIGS. 7A and 7B relate to Fc:FcγR contact interfaces. FIG. 7A is a cartoon representation of the crystal structure of the hIgG$_1$ Fc complex with hFcγRIII (PDB ID: 1E4K). FcγRIII is shown at the top of the cartoon. FIG. 7B shows the residues randomized in the Fc loop libraries used in the screen. Dark black bars represent four amino acid stretches that were completely randomized.

FIG. 13 is a Table (Table 1) depicting mutant polypeptides within the scope of the present invention.

DETAILED DESCRIPTION

Figure 1:
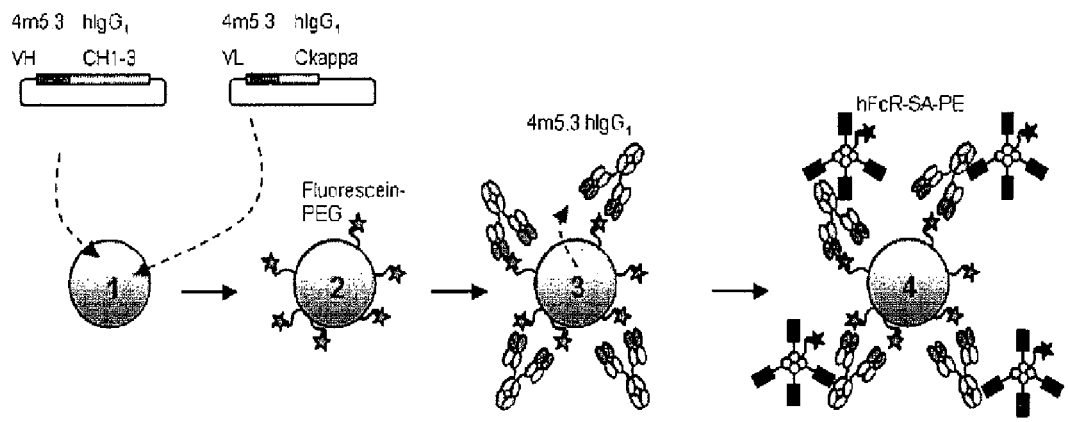
FIG. 1 is a schematic representation of full-length hIgG1 Fc displayed on yeast cells. Yeast transformed with 4m5.3 heavy chain and light chain secretion vectors are conjugated with NHS-PEG-fluorescein, then induced for secretion in PEG-containing medium. IgG variants are preferentially captured on the fluorescein-labeled yeast cell from which they were secreted (Rakestraw et al., *Biotechnol. Prog.* 22, 22:1200-1208, 2006). The displayed library is subsequently screened with preformed tetramers consisting of biotinylated soluble hFcγRs and fluorophore conjugated streptavidin (SA).
Figures 2A, 2B, 2C:
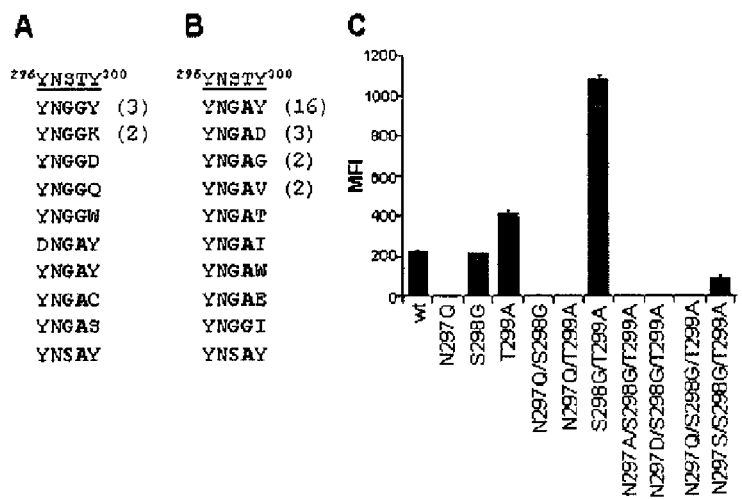
FIGS. 2A-2C depict various aglycosylated C'/E loop variants (A and B) and their ability to bind FcγRIIA.
Figure 3:
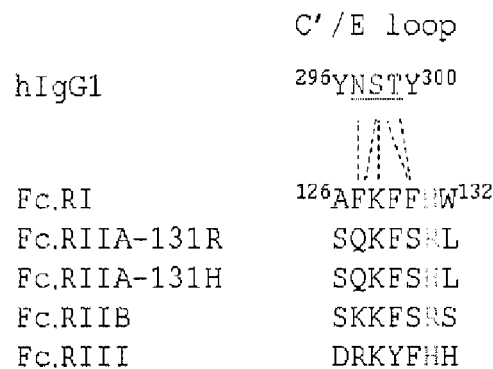
FIG. 3 is a representation of C'/E loop contacts with FcγRs. hFcγR family sequence alignment near predicted contacts with the hIgG1 C'/E loop (Sondermann et al., *J. Mol. Biol.* 309:737-749, 2001). Dotted lines represent predicted contacts between residues on the Fc and FcγR (Sondermann et al., *J. Mol. Biol.* 309:737-749, 2001).

Over the past several decades, antibody-based therapy has emerged as a promising mode of treatment of human disease, and in particular in the treatment of human cancer (Adams and Weiner, *Nat. Biotechnol.* 23:1147-1157, 2005; Reichert and Valge-Archer, *Nat. Rev. Drug Discov.* 6:349-356, 2007). While multiple mechanisms contribute to the efficacy of therapeutic antibodies (Adams and Weiner, *Nat. Biotechnol.* 23:1147-1157, 2005; Carter, *Nature Reviews Cancer* 1:118-129, 2001), activation of immune effector functions has been shown to play a critical role in the efficacy of several therapeutic antibodies, in particular through an antibody's engagement of the Fcγ receptors (FcγRs) of immune cells (Nimmerjahn and Ravetch, *Curr. Opin. Immunol.* 19:239-245, 2007). Here, as in immunity, IgGs act as the adaptor between a target cell or pathogen and the immune response by simultaneously binding antigen through their variable regions and activating an immune response through interaction of their conserved Fc regions with FcγRs on immune cells.

The human FcγR (hFcγR) family consists of the activating receptors FcγRI, FcγRIIA, and FcγRIIIA, and the inhibitory receptor FcγRIIB. While FcγRI binds IgG with high affinity (nanomolar binding constants), FcγRIIA, FcγRIIB, and FcγRIIIA bind IgG with micromolar affinity, becoming activated only via avid multivalent interactions with opsonized antigen (Nimmerjahn and Ravetch, *Nat. Rev. Immunol.* 8:34-47, 2008). In particular, the efficacy of therapeutic antibodies is strongly correlated to the allelic forms of FcγRIIIA possessed by a given individual. Populations homozygous for a valine at position 176 of FcγRIIIA (FcγRIIIA$^{176V}$), as opposed to a phenylalanine (FcγRIIIA$^{176F}$), have dramatically improved response rates (Cartron et al., *Blood* 99:754-758, 2002; Musolino et al., *J. Clin. Oncol.* 26:1789-1796, 2008; Weng et al., *J. Clin. Oncol.* 22:4717-4724, 2004; Weng and Levy, *J. Clin. Oncol.* 21:3940-3947, 2003), likely due to a several-fold stronger binding of wild-type hIgG$_1$ for the FcγRIIIA$^{176V}$ allele.

We have demonstrated that aglycosylated human IgG$_1$ Fc variants are capable of engaging a subset of the low-affinity FcγRs with approximately wild-type binding affinity and activating immune effector cells in vivo, demonstrating that N-linked glycosylation of the Fc is not a strict requirement for FcγR engagement. Numerous previous studies have shown that the binding of IgG to FcγR is highly sensitive to the presence of a single N-linked glycosylation site at asparagine 297 (N297) of the Fc, with deglycosylation resulting in a complete loss of FcγR binding (Jefferis and Lund, *Immunol. Leo.* 82:57-65, 2002; Simmons et al., *J. Immunological Methods* 263:133-147, 2002; Shields et al., *J. Biol. Chem.* 276: 6591-6604, 2001; Tao and Morrison, *J. Immunol.* 143:2595-2601, 1989; Mimura et al., *J. Biol. Chem.* 276:45539-45547, 2001; Walker et al., *Biochem J.* 259:347-353, 1989). Thus, aglycosylated variants have the potential to open up therapeutic antibody production to virtually any expression system, removing the post-translational variation in N-glycan synthesis that occurs across organisms, or in the case of the common prokaryotic expression host *E. coli*, the complete absence of N-linked glycosylation. Such variation in the nature of the N-linked glycan imparts substantial changes in the affinity to FcγR and subsequent biological response (Kaneko et al., *Science* 313:670-673, 2006; Shields et al., *J. Biol. Chem.* 277: 26733-26740, 2002), and additionally can lead to the presence of sugars that are rapidly cleared and/or immunogenic.

The compositions and methods described herein are useful for the preparation of antibodies, including antibodies useful in research and clinical settings (e.g., diagnostic and therapeutic antibodies). FcγR engagement is essential to the function of IgG in both immunity and in antibody-based therapy. IgGs act as the adaptor between a pathogen and the immune response by simultaneously binding antigen through their variable regions and activating an immune response through interaction of conserved Fc regions with FcγRs on cells of the immune system. The human FcγR (hFcγR) family consists of the activating receptors hFcγRI (RI), hFcγRIIA (RIIA), and hFcγRIIIA (RIIIA), and the inhibitory receptor hFcγRIIB (RIIB). While RI binds IgG with high affinity (nanomolar binding constants), RIIA, RIIB, and RIIIA bind IgG with micromolar affinity, becoming activated only via avid multivalent interactions with opsonized antigen. The binding of IgG to FcγR is highly sensitive to the presence of glycosylation at a single N-linked glycosylation site at Asparagine 297 (N297) in its CH2 domain, with a loss of binding to the low-affinity FcγRs observed in N297 point mutants, enzymatic Fc deglycosylation, recombinant IgG expression in the presence of the N-linked glycosylation inhibitor tunicamycin, or expression in bacteria. In addition, the nature of the carbohydrate attached to N297 modulates the affinity of the FcγR interaction, as the presence or absence of a fucose residue or a sialic acid residue alters the affinity to FcγR. Sialylation of the N-linked carbohydrate switches IgG to an anti-inflammatory binding mode, implicating a potentially key physiological role for Fc glycosylation.

In crystal structures of the complex, FcγR/Fc contact is mediated not only by protein-protein contacts, but specific interactions with the glycan on the Fc that are proposed to contribute to binding affinity. Additional intramolecular contacts are made between the Fc-linked glycan and residues on the IgG CH2 domain, and it is thought that these interactions stabilize an open Fc conformation capable of being engaged by FcγR. Successive truncation of an IgG$_1$ glycan results in an incremental loss of binding affinity and concomitant incremental collapse of the open Fc conformation. In the IgG$_1$ Fc:FcγRIII complex, extensive contacts are made by both chains of the IgG$_1$ hinge region, with additional receptor contacts made by the B/C loop, F/G loop, and both sidechains in, and glycosylation emanating from, the C'/E loop of the CH2 domain. This loop plays a part in receptor recognition through both direct sidechain contacts as well as in encoding information for a critical post-translational modification.

Antibodies:

The present antibodies, which retain Fc receptor binding activity despite having one or more mutations in the Fc region that prohibit glycosylation, can assume various configurations. For example, the antibody can be a tetramer (e.g., an antibody having two heavy chains and two light chains). Accordingly, the antibodies of the invention include proteins that may have one or two heavy (H) chain variable regions, and one or two light chain variable regions. The VHC and VLC regions can be further subdivided into regions of hypervariability, termed "complementarity determining regions" (CDRs), interspersed with regions that are more conserved, termed "framework regions" (FRs). The extent of the FRs and CDRs has been defined (see, Kabat, E. A., et al. *Sequences of Proteins of Immunological Interest*, Fifth Edition, U.S. Department of Health and Human Services, NIH Publication No. 91-3242, 1991, and Chothia, et al., *J. Mol. Biol.* 196:901-917, 1987, which are incorporated herein by reference). Where an antibody of the invention includes one or more VHCs and/or one or more VLCs, each VHC and VLC can be composed of three CDRs and four FRs, arranged from amino-terminus to carboxy-terminus in the following order: FR1, CDR1, FR2, CDR2, FR3, CDR3, FR4.

The VHC or VLC chain of an antibody of the invention can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains: CH1, CH2 and CH3. The light chain constant region is comprised of one domain: CL. The variable regions of the heavy and light chains contain a binding domain that interacts with an antigen. The constant regions of the antibodies typically mediate the binding of the antibody to host tissues or factors, including various cells of the immune system (e.g., effector cells) and the first component (C1q) of the classical complement system. The term "antibody" includes intact immunoglobulins of types IgA, IgG, IgE, IgD, IgM (as well as subtypes thereof (e.g., IgG$_1$, IgG$_2$, IgG$_3$, and IgG$_4$)), wherein the light chains of the immunoglobulin may be of types kappa or lambda.

Antibodies may also be referred to as "immunoglobulins" (proteins consisting of one or more polypeptides substantially encoded by immunoglobulin genes, the aglycosylated antibodies of the invention may also be referred to as aglycosylated immunoglobulins, and may contain sequences encoded by one or more of the human immunoglobulin genes). Single chain immunoglobulins, and chimeric, humanized or CDR-grafted immunoglobulins, as well as chimeric or CDR-grafted single chain immunoglobulins, comprising portions derived from different species, are also encompassed by the present invention and the term "immunoglobulin." The recognized human immunoglobulin genes include the kappa, lambda, alpha (IgA$_1$ and IgA$_2$), gamma (IgG$_1$, IgG$_2$, IgG$_3$, IgG$_4$), delta, epsilon, and mu constant region genes, as well as the myriad immunoglobulin variable region genes. Full-length immunoglobulin "light chains" (about 25 kDa in mass and 214 amino acids in length) are encoded by a variable region gene at the NH$_2$-terminus (about 110 amino acids) and a kappa or lambda constant region gene at the COOH-terminus. Full-length immunoglobulin heavy chains (about 50 kDa in mass and 446 amino acids in length), are similarly encoded by a variable region gene (about 116 amino acids) and one of the other aforementioned constant region genes, e.g., gamma (encoding about 330 amino acids). The antibodies or immunoglobulins of the present invention may include CDRs (which are described further herein) from a human or non-human source. The framework of the immunoglobulin can be human, humanized, or non-human, e.g., a murine framework modified to decrease antigenicity in humans, or a synthetic framework, e.g., a consensus sequence.

The term "antigen-binding portion" of an antibody (or simply "antibody portion," or "portion"), as used herein, refers to a portion of an antibody that specifically binds to an antigen, e.g., a molecule in which one or more immunoglobulin chains is not full length, but which specifically binds to an antigen.

As used herein, the term "human antibody" includes any antibody in which the framework residues correspond to human germline sequences and the CDRs result from V(D)J recombination and somatic mutations. However, human antibodies may also comprise amino acid residues not encoded in human germline immunoglobulin nucleic acid sequences (e.g., mutations introduced by random or site-specific mutagenesis in vitro). It has been demonstrated that in vivo somatic mutation of human variable genes results in mutation of framework residues (see *Nat. Immunol.* 2:537, 2001). Such an antibody would be termed "human" given its source, despite the framework mutations. Mouse antibody variable domains also contain somatic mutations in framework residues (See *Sem. Immunol* 8:159, 1996). Consequently, transgenic mice containing the human Ig locus produce antibodies that are commonly referred to as "fully human," even though they possess an average of 4.5 framework mutations (a range of 1-8 in this work: *Nat. Genet.* 15:146-156, 1997). Accepted usage therefore indicates that an antibody variable domain gene based on germline sequence but possessing framework mutations introduced by, for example, an in vivo somatic mutational process is termed "human." Thus, the invention encompasses human antibodies that specifically bind an antigen (e.g., a cancer antigen, even where those antibodies include mutations (e.g., mutations within the FR) and fragments or other variants thereof.

The antibodies can be polyclonal or monoclonal. The antibodies and antigen binding portions thereof described herein are useful in therapeutic compositions and regimens, diagnostic compositions and regimens, and in assays requiring an agent that can identify or inhibit protein implicated in a disease or disorder, e.g., cancer. The present invention encompasses an antibody or antigen binding portion thereof for use in therapy (including prophylaxis) or diagnosis (e.g., of particular diseases or conditions such as cancers), and use of such antibodies or antigen binding portions thereof for the manufacture of a medicament for use in treatment of diseases or conditions as described herein.

Chimeric, humanized or CDR-grafted antibodies, comprising portions derived from different species, are also encompassed by the present invention and the term "antibody." The various portions of these antibodies can be joined together chemically by conventional techniques, or can be prepared as contiguous polypeptides using genetic engineering techniques. For example, nucleic acids encoding a chimeric or humanized chain can be expressed to produce a contiguous polypeptide. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman et al., *BioTechnology* 10:1455-1460, 1992, regarding CDR-graft antibody, and Ladner et al., U.S. Pat. No. 4,946,778 and Bird, R. E. et al., *Science* 242: 423-426, 1988 regarding single chain antibodies.

In addition, antigen binding portions of antibodies, including fragments of chimeric, humanized, CDR-grafted or single chain antibodies, can also be produced and are within the scope of the present invention. Antigen binding portions of the antibodies retain at least one binding function of the full-length antibody from which they are derived. Useful antigen binding portions retain an antigen binding function of a corresponding full-length antibody (e.g., specificity for a cancer antigen). Functional fragments can retain the ability of the full-length antibody to inhibit one or more functions characteristic of a cancer antigen or a cell expressing a cancer antigen.

A cancer antigen is a molecule (e.g., a polypeptide, carbohydrate or lipid) that is expressed by a cancer cell and either (a) differs qualitatively from its counterpart expressed in normal cells, or (b) is expressed at a higher level in cancer cells than in normal cells. Thus, a cancer antigen can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart. Examples of relevant cancers include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such ovarian cancer, vaginal cancer, bladder cancer, testicular cancer, prostate cancer or penile cancer, bone tumors, and vascular tumors. Examples of cancer antigens include, without limitation, carcinoembryonic antigen (CEA), RAGE, MART (melanoma antigen), MAGE (melanoma antigen) 1-4, 6 and 12, MUC (mucin) (e.g., MUC-1, MUC-2, etc.), tyrosinase, Pmel 17 (gp100), GnT-V intron V sequence (N-acetylglucoaminyltransferase V intron V sequence), Prostate cancer psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP) Bc1-2, prostate specific antigen (PSA), and Ki-67.

The invention provides chimeric antibodies that can be prepared as a contiguous polypeptide using genetic engineering techniques (e.g., DNA encoding the protein portions of the chimeric antibody can be expressed to produce a contiguous polypeptide chain). One example of a chimeric antibody of the present invention is an antibody containing one or more antibody chains comprising a CDR (e.g., one or more CDRs of an antibody described herein) and a framework region derived from a light and/or heavy chain of a second antibody (e.g., of human origin; e.g., CDR-grafted antibodies with or without framework changes). Chimeric or CDR-grafted antibodies also include humanized immunoglobulin. See, e.g., Cabilly et al., U.S. Pat. No. 4,816,567; Cabilly et al., European Patent No. 0,125,023 B1; Queen et al., European Patent No. 0,451,216 B1; Boss et al., U.S. Pat. No. 4,816,397; Boss et al., European Patent No. 0,120,694 B1; Neuberger et al., WO 86/01533; Neuberger et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778 and Huston, U.S. Pat. No. 5,476,786.

Chimeric antibodies can be produced using synthetic and/or recombinant nucleic acids to prepare genes (e.g., cDNA) encoding the desired chimeric chain. For example, nucleic acid (e.g., DNA) sequences coding for variable regions can be constructed using PCR mutagenesis methods to alter DNA sequences encoding an antibody chain, e.g., using methods employed to generate humanized antibodies (see e.g., Kanunan, et al., *Nucl. Acids Res.* 17:5404, 1989; Sato, et al., *Cancer Research* 53: 851-856, 1993; Daugherty, et al., *Nucleic Acids Res.* 19(9): 2471-2476, 1991; and Lewis and Crowe, *Gene* 101: 297-302, 1991). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

Other suitable methods of producing or isolating antibodies include, for example, methods that rely upon immunization of transgenic animals (e.g., mice) capable of producing a full repertoire of human antibodies (see e.g., Jakobovits et al., *Proc. Natl. Acad. Sci. USA* 90: 2551-2555, 1993; Jakobovits et al., *Nature* 362: 255-258, 1993; Lonberg et al., U.S. Pat. No. 5,545,806; Surani et al., U.S. Pat. No. 5,545,807).

Antibodies that specifically bind to an antigen, e.g., a cancer antigen, can be identified by expressing recombinant antibodies in a library and selecting members of the library that bind the antigen. The affinity of the selected antibodies for the antigen can be further enhanced by affinity-maturing these antibodies, e.g., using PCR mutagenesis, chain shuffling, or CDR shuffling techniques in conjunction with one or more cycles of screening, as described herein. Other methods can also be used to generate anti-cancer antigen antibodies. For example, such antibodies can be produced by immunizing animals. A variety of methods have been described for preparing antigen for immunization and for generating monoclonal antibodies from immunized animals (see e.g., Kohler et al., *Nature* 256:495-497, 1975; Kohler and Milstein, *Eur. J. Immunol.* 6:511-519, 1976; Milstein et al., *Nature* 266:550-552, 1977; Koprowski at al., U.S. Pat. No. 4,172,124; Harlow, E. and D. Lane, 1988, Antibodies: A Laboratory Manual, (Cold Spring Harbor Laboratory Press: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line) with antibody producing cells. The antibody producing cell, preferably those of the spleen or lymph nodes, are obtained from immunized animals. The fused cells (hybridomas) can be isolated using selective culture conditions and cloned by limiting dilution. Cells that produce antibodies with the desired specificity can be selected by a suitable assay (e.g., ELISA).

Specifically binding immunoglobulins can be immunoglobulins that 1) exhibit a threshold level of binding activity and/or 2) do not significantly cross-react with known related polypeptide molecules. The binding affinity of an immunoglobulin can be readily determined by one of ordinary skill in the art, for example, by Scatchard analysis (Scatchard, *Ann. NY Acad. Sci.* 51 660-672, 1949).

For example, the immunoglobulins can bind with high affinity of $10^{-4}$ M or less, $10^{-7}$ M or less, $10^{-9}$ M or less or with subnanomolar affinity (0.9, 0.8, 0.7, 0.6, 0.5, 0.4, 0.3, 0.2, 0.1 nM or even less). Immunoglobulins may also be described or specified in terms of their binding affinity for their specific cellular targets. For example, binding affinities include those with a $K_d$ less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M, or less.

As used herein, the term "substantially identical" (or "substantially homologous") refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the first antibody.

Calculations of "homology" or "identity" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In different embodiments, the length of a reference sequence aligned for comparison purposes is at least 50% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences is determined using the Needleman and Wunsch, *J. Mol. Biol.* 48:444-453, 1970, algorithm which has been incorporated into the GAP program in the GCG software package, using a BLOSUM 62 scoring matrix with a gap penalty of 12, a gap extend penalty of 4, and a frameshift gap penalty of 5.

In addition to the mutations described herein, it is to be understood that the antibodies and antigen binding portions of the present antibodies may have additional conservative or non-essential amino acid substitutions (a "non-essential" amino acid residue is a residue that can be altered from the wild-type sequence of a polypeptide, such as a binding agent, e.g., an antibody, without substantially altering a biological activity, whereas an "essential" amino acid residue results in such a change).

Whether or not a particular substitution will be tolerated, i.e., will not adversely affect desired biological properties, such as binding activity, can be determined as described in Bowie et al., *Science,* 247:1306-1310, 1990. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The Fc regions of the invention, e.g., an Fc region with favorable effector functions and also optionally favorable pharmacokinetics, can also be linked to one or more molecules. The linkage may be synthetic in nature, e.g., via chemical conjugation, or via recombinant expression, e.g., a fusion polypeptide is formed. Thus, the molecule linked to an Fc region may be a molecule useful to isolate or purify the Fc region, e.g., a tag such as a FLAG-tag, Strep-tag, glutathione S transferase, maltose binding protein (MBP) or a His-tag, or other heterologous polypeptide and/or another molecule, e.g., a ligand for a receptor, an extracellular domain of a receptor, a variable region of a heavy Ig chain, a toxin, a radioisotope or a chemotherapeutic. A heterologous polypeptide is a polypeptide that is not naturally (in nature) associated with a particular Fc region and optionally binds a target molecule. For instance, the heterologous polypeptide may be an enzyme, a receptor, e.g., an extracellular domain of a receptor, or other protein or protein domain that binds another (target) molecule. The heterologous polypeptide of the fusion may correspond to a full-length (wild-type) polypeptide or a target-binding fragment thereof. A heterologous polypeptide may have a sequence that differs from that of a corresponding native (wild-type) or parent polypeptide sequence by virtue of at least one amino acid substitution, e.g., from about one to about twenty amino acid substitutions, i.e., it is a variant heterologous polypeptide, but has substantially the same activity, e.g., substantially the same target binding activity, as the corresponding native or parent polypeptide. A variant polypeptide sequence has at least about 80% homology with a wild-type or parent polypeptide sequence, and most preferably at least about 90% homology, more preferably at least about 95% homology, with a wild-type or parent polypeptide sequence.

Methods to screen for various activities associated with an Fc region as well as activities associated with polypeptides or complexes that incorporate an Fc region, activities including but not limited to FcR binding (see U.S. Pat. No. 6,737,056 and U.S. published application Serial No. US 2004/013210) are well known in the art.

Fc Receptors:

FcRs are defined by their specificity for immunoglobulin isotypes. For example, FcRs for IgG antibodies are referred to as FcγR those for IgR as FcεR, and those for IgA as FcαR. Another type of FcR is the neonatal FcR (FcRn). In humans, the FCRs for the IgG class include FcγRI (CD64), including isoforms FcγRIA, FcγRIb, and FcγRIc; FcγRII (CD32), including isoforms FcγRIIa (including allotypes H131 and R131), FcγRIIb (including FcγRIIb-1 and FcγRIIb-2), and FcγRIIC; and FcγRIII (CD16), including isoforms FcγRIIa (including alloytypes V158 and F158) and FcγRIIIb (including allotyped FcγRIIIb-NA1 and FcγRIIIb-NA2). Mouse FcγRs include but are not limited to FcγRI (CD64), FcγRII (CD32), FcγRIII (CD16), and FcγRIV (CD16-2). FcγRI, FcγRIIa/c, and FcγRIIa are positive regulators of immune complex triggered activation, characterized by having an intracellular domain that has an immunoreceptor tyrosine-based activation motif (ITAM), while FcγRIIb has an immunoreceptor tyrosine-based inhibition motif (ITIM) and is therefore inhibitory.

FCRs are expressed in a variety of immune cells including monocytes, macrophages, neutrophils, dendritic cells, eosinophils, mast cells, platelets, B cells large granular cells, natural killer (NK) cells and γγ cells, Formation of the Fc/FcγR complex recruits these effectors cells stand subsequent immune response such as release of inflammation mediators, B cell activation, endocytosis, phagocytosis, and cytotoxic attack, The cell-mediated reaction where nonspecific cytoxic cells that express FcγRs recognize bound antibody on a target cell and subsequently cause lyses of the target cell is referred to as DACCA Examples of human leukocytes that mediate DACCA include peripheral blood mononuclear cells (PMBC), natural killer (NK) cells, monocytes, cyotoxic T cells and neutrophils, with PBMCs and NK cell being proffered. The effector cells may be isolated form a native source e.g. from proffered. The effector cells may be isolated from a native source, e.g., from blood or PBMCs, including cells cultured from blood or fractions thereof; or may be permanent cell lines.

Most FcγRs bind the same region on IgG Gc, at the N-terminal end of Cγ domain and the preceding hinge. In particular, the binding site on IgG for FcγR likely includes residues in the lower hinge region, i.e., residues 233-239 (EU index numbering as in Kabat et al., supra), although other regions may be involved in binding. e.g., G316-K338 (human IgG for human FcγRI), K274-R301 (human IgG1 for human FcγRIII), Y407-R416 (human IgG for human FcγRIII), as well as N297 and E318 (murine IgG2b for murine FcγII). FcRs may bind Fc regions of the same isotype with different activities. For instance, IgG1 and IgG3 typically bind substantially better for FcγRs than IfG2 and IgG4. FcR also differ in expression pattern and level on different immune cells. For example, in humans, FcγRIIIB is found only on neutrophils, whereas FcγRIIIA is found on macrophages, monocytes, natural killer (NK) cells and a subpopulation of T-cells, FcγRIIIA is the only FcR present on NK cells, one of the cell types implicated in ADCC, moreover, there are a number of FcγR polymorphisms, some of which are associated with higher binding affinities. Further, efficient Fc binding to FcγR is associated with N-linked glycosylation at position 297, and alterations in the composition of the N297 carbohydrate or its elimination affects FcR binding.

Nucleic Acids:

The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode an antibody, an Fc fragment, and Fc fusion protein or a conjugate thereof.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein (i.e. an antibody or an Fc sequence). PCR can be used to amplify specific sequences from DNA as well as RNA, including sequences from total genomic DNA or total cellular RNA. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid (as one may wish to do, for example, when making a variant of a fragment of an antibody, an Fc fragment, and Fc fusion protein or a conjugate thereof).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., an antibody, an Fc fragment, and Fc fusion protein or a conjugate thereof).

Two nucleic acids or the polypeptides they encode may be described as having a certain degree of identity to one another. For example, a fragment of an antibody, an Fc fragment, and Fc fusion protein or a conjugate thereof and a biologically active variant thereof may be described as exhibiting a certain degree of identity. Alignments may be assembled by locating short antibody, or Fc sequences in the Protein Information Research (PIR) site. (http://pir.georgetown.edu) followed by analysis with the "short nearly identical sequences" Basic Local Alignment Search Tool (BLAST) algorithm on the NCBI website (http://www.ncbi.nlm.nih.gov/blast).

As used herein, the term "percent sequence identity" refers to the degree of identity between any given query sequence and a subject sequence. For example, a naturally occurring antibody, or Fc sequence can be the query sequence and a fragment of an antibody, or Fc sequence precursor protein can be the subject sequence. Similarly, a fragment of an antibody, or Fc sequence can be the query sequence and a biologically active variant thereof can be the subject sequence.

To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., *Nucleic Acids Res.* 31:3497-3500, 2003.

The nucleic acids and polypeptides described herein may be referred to as "exogenous" to indicate that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express an antibody, or Fc sequence. A recombinant nucleic acid construct comprises a nucleic acid encoding an antibody, or Fc sequence as described herein, operably linked to a regulatory region suitable for expressing the antibody or Fc sequence in the cell. Thus, a nucleic acid can comprise a coding sequence that encodes any of the Fc sequences as set forth in the Examples. In some cases, a recombinant nucleic acid construct can include a nucleic acid comprising a coding sequence, a gene, or a fragment of a coding sequence or gene in an antisense orientation so that the antisense strand of RNA is transcribed. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for a given antibody or Fc sequence can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Diagnostic and Therapeutic Applications:

The antibodies of the present invention are useful in a variety of applications, including research, diagnostic and therapeutic applications. The methods disclosed herein can be applied to a wide range of species, e.g., humans, non-human primates (e.g., monkeys), horses, cattle, pigs, sheep, deer, elk, goats, dogs, cats, mustelids, rabbits, guinea pigs, hamsters, rats, and mice. The engineered proteins described herein are useful in therapeutic compositions and regimens or for the manufacture of a medicament for use in treatment of diseases or conditions as described herein. In one embodiment, the antibodies are labeled with a suitable label (e.g., fluorescent label, chemiluminescent label, isotope label, epitope or enzyme label).

For example, antibodies or antigen binding portions thereof that block and/or inhibit the activity of a cancer antigen can be used to inhibit cell transformation and/or to diagnose transformed cells. Therapeutic use of an antibody or antigen binding portion thereof includes prophylactic use (e.g., for treatment of a patient who may be at risk for developing a cancer). The antibodies can be administered in combination with one or more other therapeutic agents such as an anti-cancer agent. Nonlimiting examples of anti-cancer agents include, e.g., antimicrotubule agents, topoisomerase inhibitors, antimetabolites, mitotic inhibitors, alkylating agents, intercalating agents, agents capable of interfering with a signal transduction pathway, agents that promote apoptosis (including cell death genes), radioactive compounds, and antibodies against other tumor-associated antigens (including naked antibodies, immunotoxins and radioconjugates).

Modes of Administration:

According to the method, one or more antibodies or antigen binding portions thereof can be administered to the host by an appropriate route, either alone or in combination with (before, simultaneous with, or after) another drug. For example, the antibodies of the present invention can also be used in combination with other monoclonal or polyclonal antibodies or with chemotherapeutic treatments. The antibodies disclosed herein are generally useful for as prophylactic vaccines or immune response-stimulating therapeutics. As used herein, "prophylaxis" can mean complete prevention of the symptoms of a disease, a delay in onset of the symptoms of a disease, or a lessening in the severity of subsequently developed disease symptoms. As used herein, "therapy" can mean a complete abolishment of the symptoms of a disease or a decrease in the severity of the symptoms of the disease.

The antibodies described herein can be administered directly to a mammal. Generally, the antibodies can be suspended in a pharmaceutically acceptable carrier (e.g., physiological saline or a buffered saline solution) to facilitate their delivery. Encapsulation of the polypeptides in a suitable delivery vehicle (e.g., polymeric microparticles or implantable devices) may increase the efficiency of delivery. A composition can be made by combining any of the peptides provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants (e.g., propyl gallate), chelating agents, inert gases, and the like may also be present. It will be appreciated that any material described herein that is to be administered to a mammal can contain one or more pharmaceutically acceptable carriers.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinician. Suitable dosages are in the range of 0.01-1,000 µg/kg Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the engineered proteins in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, an engineered protein can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present engineered proteins can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. For example, an effective amount can be an amount sufficient to achieve the desired therapeutic effect, under the conditions of administration, such as an amount sufficient for inhibition of the function of a cancer antigen, and thereby, inhibition of a tumor cell. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

Alternatively, a polynucleotide containing a nucleic acid sequence encoding an antibody can be delivered to an appropriate cell of the animal. This can be achieved by, for example, the use of a polymeric, biodegradable microparticle or microcapsule delivery vehicle, sized to optimize phagocytosis by phagocytic cells such as macrophages. For example, PLGA (poly-lactide-co-glycolide) microparticles approximately 1-10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 µm and preferably larger than 20 µm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the antibody with an initiator methionine and optionally a targeting sequence is operatively linked to a promoter or enhancer-promoter combination. Promoters and enhancers are described above, and many are well known in the art.

Polynucleotides can be administered in a pharmaceutically acceptable carrier. Pharmaceutically acceptable carriers are biologically compatible vehicles which are suitable for administration to a human or other mammalian subject (e.g., physiological saline). A therapeutically effective amount is an amount of the polynucleotide which is capable of producing a medically desirable result (e.g., a decrease in clinical motor symptoms) in a treated mammal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed.

A variety of routes of administration are possible including, but not necessarily limited to, parenteral (e.g., intravenous, intraarterial, intramuscular, subcutaneous injection), oral, dietary, topical, inhalation (e.g., intrabronchial, intranasal or oral inhalation, intranasal drops), depending on the disease or condition to be treated. Other suitable methods of administration can also include rechargeable or biodegradable devices and slow release polymeric devices. The pharmaceutical compositions described herein can also be administered as part of a combinatorial therapy with other agents.

As noted, the Fc variants or polypeptides incorporating an Fc variant may be used to prevent, inhibit or treat various conditions or diseases, in humans and non-humans, including non-human mammals. For example, an antibody containing a modified Fc region of the invention may be administered to a human or non-human animal which is at risk of, e.g., prone to having a disease, prior to the onset of the disease and so prevent or inhibit one or more symptoms of that disease. An Fc region or Fc region containing polypeptide, or a conjugate thereof, may be administered after clinical manifestation of a disease in a human or non-human animal to inhibit or treat the disease. In one embodiment, a pharmaceutical composition comprising an antibody or Fc fusion polypeptide of the present invention can be administered to a human or non-human animal with a neoplastic disease, e.g., cancer. Examples of cancer which may be inhibited or treated with an Fc containing polypeptide of the invention, include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

Pharmaceutical compositions are also contemplated having an Fc region, an Fc fusion polypeptide, antibodies having an Fc region, or conjugates thereof, that are formulated, optionally with one or more other agents. The compositions can include one or more antibodies, or Fc regions, e.g., 2, 3, 4, 5, 6 or more antibodies. Formulation of an antibody or portion thereof to be administered will vary according to the route of administration selected (e.g., solution, emulsion, capsule). An appropriate pharmaceutical composition comprising an antibody or antigen binding portion thereof to be administered can be prepared in a physiologically acceptable vehicle or carrier. A mixture of antibodies and/or portions can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the compound can be solubilized and loaded into a suitable dispenser for administration (e.g., an atomizer, nebulizer or pressurized aerosol dispenser).

Formulations of antibodies, Fc regions, or Fc region containing polypeptides, or conjugates of the present invention are prepared for storage by mixing the antibodies, Fc regions, or Fc region containing polypeptides, or conjugates, having the desired degree of purity with optional pharmaceutically acceptable carriers, excipients or stabilizers in the form of lyophilized formulations or aqueous solutions. Acceptable carriers, excipients, or stabilizers are nontoxic to recipients at the dosages and concentrations employed, and include buffers such as antioxidants; alkyl parabens; low molecular weight (less than about 10 residues) polypeptides; hydrophilic polymers; amino acids; monosaccharides; and other carbohydrates; chelating agents; fillers; binding agents; additives; coloring agents; salt-forming counter-ions; metal complexes; and/or non-ionic surfactants. Other formulations include lipid or surfactant based formulations, microparticle or nanoparticle based formulations, including sustained release dosage formulations, which are prepared by methods know in the art.

The concentration of the Fc region, antibody or other Fc region containing polypeptide of the present invention in the formulation may vary from about 0.1 to 100 weight %. In a preferred embodiment, the concentration of the Fc region, antibody or Fc fusion polypeptide is in the range of 0.001 to 2.0 M. In order to treat a patient, an effective dose of the Fc region, or antibody or other Fc region containing polypeptide, and conjugates thereof, of the present invention may be administered. By "therapeutically effective dose" herein is meant a dose that produces the effects for which it is administered. Dosages may range from 0.01 to 100 mg/kg of body weight or greater, for example 0.1, 1, 10, or 50 mg/kg of body weight, with 1 to 30 mg/kg being preferred, although other dosages may provide beneficial results, e.g., in diagnostic applications. The amount administered is selected to prevent treat a particular condition or disease.

The antibodies of the invention can also be administered with another therapeutic agent, such as a cytotoxic agent, or cancer chemotherapeutic. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In some embodiments the methods provided contemplate the administration of combinations, or "cocktails", of different antibodies. Such antibody cocktails may have certain advantages inasmuch as they contain antibodies which exploit different effector mechanisms or combine directly cytotoxic antibodies with antibodies that rely on immune effector functionality. Such antibodies in combination may exhibit synergistic therapeutic effects. Useful antibodies can include antibodies that target the EGF receptor, e.g., Cetuximab (Erbitux™), antibodies that target VEGF, e.g., Bevacizumab (Avastin™) and antibodies that target Her-2, e.g., trastuzimab (Herceptin™)

A cytotoxic agent refers to a substance that inhibits or prevents the function of cells and/or causes destruction of cells. The term is intended to include radioactive isotopes (e.g., $^{131}$I, $^{125}$I, $^{90}$Y and $^{186}$Re), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody disclosed herein.

In some embodiments, conventional cancer medicaments are administered with the compositions disclosed herein. Suitable agents include those agents that promote DNA-damage, e.g., double stranded breaks in cellular DNA, in cancer cells. Any form of DNA-damaging agent know to those of skill in the art can be used. DNA damage can typically be produced by radiation therapy and/or chemotherapy. Examples of radiation therapy include, without limitation, external radiation therapy and internal radiation therapy (also called brachytherapy). Energy sources for external radiation therapy include x-rays, gamma rays and particle beams; energy sources used in internal radiation include radioactive iodine (iodine$^{125}$ or iodine$^{131}$), and from strontium$^{89}$, or radioisotopes of phosphorous, palladium, cesium, iridium, phosphate, or cobalt. Methods of administering radiation therapy are well know to those of skill in the art.

Examples of DNA-damaging chemotherapeutic agents include, without limitation, Busulfan (Myleran), Carboplatin (Paraplatin), Carmustine (BCNU), Chlorambucil (Leukeran), Cisplatin (Platinol), Cyclophosphamide (Cytoxan, Neosar), Dacarbazine (DTIC-Dome), Ifosfamide (Ifex), Lomustine (CCNU), Mechlorethamine (nitrogen mustard, Mustargen), Melphalan (Alkeran), and Procarbazine (Matulane)

Other cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, etoposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxin®), Schizophyllan, cytarabine (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, carminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-13, mepitiostane, mitobronitol, melphalan, laminin peptides, lentinan, Coriolus versicolor extract, tegafur/uracil, estramustine (estrogen/mechlorethamine), thalidomide, and lenalidomide (Revlimid®).

Other suitable chemotherapeutics include proteasome inhibiting agents. Proteasome inhibitors block the action of proteasomes, cellular complexes that degrade proteins, particularly those short-lived proteins that are involved in cell maintenance, growth, division, and cell death. Examples of proteasome inhibitors include bortezomib (Velcade®), lactacystin (AG Scientific, Inc., San Diego, Calif.), MG132 (Biomol International, Plymouth Meeting, Pa.) PS-519, eponemycin, epoxomycin, aclacinomycin A, the dipeptide benzamide, CVT-63417, and vinyl sulfone tripeptide proteasome inhibitors.

Additional agents which may be used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues, and gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α and β); invasion inhibiting factor-2 (IIF-2); bone morphogenetic proteins 1-7 (BMP 1-7); somatostatin; thymosin-α-1; γ-globulin; superoxide dismutase (SOD); complement factors; and anti-angiogenesis factors.

A prodrug is a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, b-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

EXAMPLES

Example 1

Engineering Aglycosylated IgG Variants that Productively Engage Fc Gamma Receptors Fcγ receptor (FcγR) engagement is essential to the function of immunologlobulin G (IgG) in both immunity (Nimmerjahn and Ravetch, *Nat. Rev. Immunol.* 8:34-47, 2008) and in antibody-based therapy (Nimmerjahn and Ravetch, *Curr. Opin. Immunol.* 19:239-245, 2007; Desjarlais et al., *Drug Discov. Today* 12:898-910, 2007). IgGs act as the adaptor between a pathogen and the immune response by simultaneously binding antigen through their variable regions and activating an immune response through interaction of conserved Fc regions with FcγRs on cells of the immune system. The human FcγR (hFcγR) family consists of the activating receptors FcγRI, FcγRIIA, and FcγRIIIA and the inhibitory receptor FcγRIIB. While FcγRI binds IgG with high affinity (nanomolar binding constants), FcγRIIA, FcγRIIB, and FcγRIIIA bind IgG with micromolar affinity, becoming activated only via avid multivalent interactions with opsonized antigen (Nimmerjahn and Ravetch, *Nat. Rev. Immunol.* 8:34-47, 2008). The binding of IgG to FcγR is highly sensitive to the presence of glycosylation at a single N-linked glycosylation site at asparagine 297 (N297) in its CH2 domain (Jefferis and Lund, *Immunol. Lett.* 82:57-65, 2002; Arnold et al., *Annu. Rev. Immunol.* 25:21-50, 2007), with a loss of binding to the low-affinity FcγRs observed in N297 point mutants (Shields et al., *J. Biol. Chem.* 276:6591-6604, 2001; Tao and Morrison, *J. Immunol.* 143:2595-2601, 1989), enzymatic Fc deglycosylation (Mimura et al., *J. Biol. Chem.* 276:45539-45547, 2001), recombinant IgG expression in the presence of the N-linked glycosylation inhibitor tunicamycin (Walker et al., *Biochem. J.* 259:347-353, 1989), or expression in bacteria (Mazor et al., *Nat. Biotechnol.* 25:563-565, 2007; Simmons et al., *J. Immunol. Methods* 263:133-147, 2002). In addition, the nature of the carbohydrate attached to N297 modulates the affinity of the FcγR interaction (Kaneko et al., *Science* 313: 670-673, 2006; Shields et al., *J. Biol. Chem.* 277:26733-26740, 2002). The sensitivity of FcγR binding to specific glycoforms has limited therapeutic antibody biomanufacture to mammalian expression systems, and has led to the development of glycosylation-engineered mammalian cell lines (Shields et al., *J. Biol. Chem.* 277:26733-26740, 2002, Yamane-Ohnuki et al., *Biotechnol. Bioeng.* 87:614-622, 2004) and microbial strains with humanized glycosylation (Li, et al., *Nat. Biotechnol* 24:210-215, 2006) as methods of enhancing antibody cytotoxicity.

In crystal structures of the complex, FcγR/Fc contact is mediated not only by protein-protein contacts, but also by specific interactions with the glycan on the Fc that are proposed to contribute to binding affinity (Radaev et al., *J. Biol. Chem.* 275:16469-16477, 2001; Sondermann et al., *Nature* 406:267-273, 2000). Additional intramolecular contacts are made between the Fc-linked glycan and residues on the IgG CH2 domain, and it is thought that these interactions stabilize an open Fc conformation capable of being engaged by FcγR (Jefferis and Lund, *Immunol. Lett.* 82:57-65, 2002). Successive truncation of an $IgG_1$ glycan results in an incremental loss of binding affinity (Mimura et al., *J. Biol. Chem.* 276: 45539-45547, 2001) and concomitant incremental collapse of the open Fc conformation (Krapp et al., *J. Mol. Biol.* 325:979-989, 2003). However, glycosylation is not strictly required for engagement of all immunoglobulin receptors with their corresponding Fc ligands, notably in the binding of IgE Fc to IgεR (Basu et al., *J. Biol. Chem.* 268:13118-13127, 1993). Interestingly, the IgE Fc adopts a similar mode of binding to FcR as the $IgG_1$ Fc in the $IgG_1$ Fc:FcγRIII complex and both receptors and Fc's share structural similarity (Garman et al., *Nature* 406:259-266, 2000). In the $IgG_1$ Fc:FcγRIII complex, extensive contacts are made by both chains of the $IgG_1$ hinge region, with additional receptor contacts made by the B/C loop, F/G loop, and both sidechains and glycosylation of the C'/E loop of the CH2 domain (Radaev et al., *J. Biol. Chem.* 275:16469-16477, 2001; Sondermann et al., *Nature* 406:267-273, 2000). It is particularly striking that this loop plays a part in receptor recognition through both direct side chain contacts as well as in encoding information for a critical post-translational modification.

In the study described below, we reasoned that by optimizing the protein-protein interactions about the C'/E loop:FcγR interface at the expense of glycosylation, we could identify aglycosylated $IgG_1$ variants that maintain engagement to FcγRs. Here, we demonstrate that a small subset of substitutions at both N297 and T299 of the glycosylation motif lead to aglycosylated Fc regions that maintain engagement of FcγRs, and in a particular example are proven active in vivo.

Screening for Aglycosylated Fc Variants that Bind hFcγRIIA:

To determine if glycosylation of the Fc was an absolute requirement for FcγR engagement by $hIgG_1$, we constructed saturation mutagenesis libraries at the Fc C'/E loop and screened them by displaying the full-length IgG variants on the yeast cell surface (FIG. 1). In this display system, the femtomolar affinity fluorescein-binding 4m5.3 single-chain antibody (Boder et al., *Proc. Natl. Acad. Sci. USA* 97:10701-10705, 2000) was reformatted as a $hIgG_1$, allowing 4m5.3 $hIgG_1$ library variants to be captured on fluorescein-labeled yeast from which they are secreted, by using a cell surface secretion capture assay (Rakestraw et al., *Biotechnol. Prog.* 22, 22:1200-1208, 2006) in conjunction with an engineered leader sequence that allows for the improved secretion of fully-assembled $hIgG_1$ from *S. cerevisiae*. Three saturation libraries centered about the C'/E loop—theoretically encoding all amino acid combinations at residues 296-299, 297-299, and 297-300—were pooled and screened for binding to fluorophore labeled tetramers of a soluble form of the $FcγRIIA^{131R}$ allele by multiple rounds of fluorescence activated cell sorting (FACS).

Using this screening strategy, in addition to glycosylated variants and the wild type clone, mutants lacking the canonical Asn-X-Ser/Thr N-linked glycosylation motif were enriched from the C'/E loop libraries for binding to FcγRIIA (FIG. 2A). After two rounds of screening, three aglycosylated motifs were identified: the double mutants S298G/T299A, S298G/T299G and the single mutant T299A. After a third round of screening at increased stringency, the sublibrary was dominated by the S298G/T299A variant, suggesting it as the highest-affinity RIIA binding motif in the library (FIG. 2B).

To study the contributions of the S298G and T299A mutations to receptor binding, a series of point mutants were constructed, secreted from yeast, and assayed for their ability to bind to $FcγRIIA^{131R}$ (FIG. 2C). Both the S298G and T299A mutations alone retain binding to RIIA at comparable or increased levels to wild-type $IgG_1$, and the S298G mutation in the aglycosylated T299A background yields a variant capable of binding FcγRIIA to a much greater extent. The S298G/T299A double mutant is incapable of rescuing binding in the N297Q, N297D, and N297A backgrounds, suggesting there is a strong requirement for asparagine at position 297 for FcγRIIA binding even in the absence of conjugated carbohydrate, a finding consistent with its conservation in the initial library screen.

S298G/T299A is Aglycosylated and Binds to hFcγRs:

To confirm that the potential aglycosylated motifs identified from the yeast-based screen indeed lacked the N-linked glycan and were capable of engaging FcγRs, wild-type, S298G/T299A, and the non-receptor binding N297Q aglycosylated control were expressed and purified from HEK 293 cells. Both N297Q and S298G/T299A exhibit increased mobility by reducing SDS-PAGE and critically, are not recognized by the mannose-specific lectin LCA, consistent with the expected absence of N-linked glycosylation. Surface Plasmon Resonance (SPR) measurements show that S298G/T299A binds to both RIIA alleles, $FcγRIIA^{131R}$ and $FcγRIIA^{131H}$, and to FcγRIIB; however, this mutant does not bind to FcγRIIA nor the complement component C1q and binding to FcγRI was weakened by 10-fold. S298G/T299A binds $FcγRIIA^{131R}$ with a dissociation constant (IQ) of 1.7 μM, approximately three-fold stronger than wild-type Fc, and binds $FcγRIIA^{131H}$ with a $K_d$ of 7.0 μM, slightly weaker than wild type. A small increase in affinity compared to wild type for FcγRIIB was also observed, suggesting a preferential binding of FcγR with an arginine at position 131 (FIG. 3).

To determine whether S298G/T299A can engage native FcγRs as expressed on the cell surface, CHO cell lines stably transfected with $FcγRIIA^{131R}$, $FcγRIIA^{131H}$, and FcγRIIB were labeled with 4m5.3 $hIgG_1$ immune complexes (ICs). Both wild-type and S298G/T299A IgG ICs label all receptor-expressing CHO cells in a concentration dependent manner, demonstrating that S298G/T299A binds FcγRs in this context as well. Consistent with the soluble binding measurements, S298G/T299A IgG ICs label $FcγRIIA^{131R}$ and FcγRIIB expressing CHO cells at similar levels as wild type; however, S298G/T299A shows only intermediate labeling of the $FcγRIIA^{131H}$ allele compared to wild type and the aglycosylated control.

S298G/T299A Activates hFcγRIIA In Vivo:

To determine whether this aglycosylated IgG is functional in vivo, a murine platelet clearance model was used to test the extent of S298G/T299A activity. The platelet integrin antigen-binding antibody 6A6 was reformatted as a mouse-human IgG$_1$ chimera and the S298G/T299A mutations subsequently introduced into the human Fc domain. The antibody was tested in a transgenic mouse model in which the endogenous murine FcγRs have been deleted by gene targeting and the human activation FcγR, hFcγRIIA$^{131R}$, is expressed as a transgene, thus maintaining cell type expression appropriate for the human transgene (McKenzie et al., *J. Immunol.* 162: 4311-4318, 1999). Mice with this genotype were treated with wild-type, N297A, and S298G/T299A 6A6 hIgG$_1$ purified from HEK 293 cells and the extent of platelet clearance measured over time. After four hours, S298G/T299A-6A6 treated mice (n=3) showed a statistically significant drop in platelet count when compared to those treated with N297A-6A6 or PBS, exhibiting a response that was comparable to wild-type-6A6 and demonstrating the ability of S298G/T299A to productively engage hRIIA in vivo and result in platelet clearance.

Model of S298G/T299A-hFcγRIIA Interaction:

To explore the structural basis for FcγR binding of this aglycosylated Fc domain variant, we constructed homology models of Fc:FcγRIIA complexes based on the previously solved structures of the IgG$_1$ Fc, the FcγRIIA structure (Maxwell et al., *Nat. Struct. Biol.* 6:437442, 1999) and the Fc:FcγRIII complex (Sondermann et al., *Nature* 406:267-273, 2000). Three features emerge from this modeling. First, in the model of the wild-type interaction, there is only limited interaction between the two N-linked glycans and FcγRIIA. The asymmetric nature of the IgG$_1$ Fc: FcγRIIA interaction predicts that the glycan attached to the B chain of the Fc dimer may interact with residues K117, T119, F121, 5126, and F129 of the receptor, whereas the glycan attached to the other chain (the A chain) does not make contact with FcγRIIA. These glycan:FcγR contacts provide negligible calculated screened electrostatic intermolecular interactions (approximately zero kcal/mol), compared to the much larger intramolecular ones between glycan and Fc (roughly −1.3 kcal/mol, with a dominant contribution from N297/glycan(B)-D265(B)) and suggest that both oligosaccharides are primarily interacting with their respective Fc chains. Second, N297 is important for the Fc:FcγRIIA interaction. Aglycosylated N297 has the potential to make hydrogen bond interactions across the interface with S126 of the receptor. These interactions may be mediated by a bridging water molecule that can be observed nearby in an unbound FcγRIIA crystal structure (Maxwell et al., *Nat. Struct. Biol.* 6:437-442, 1999). Replacement of N297 with glutamine or alanine disrupts this interaction (and fails to make similar, stabilizing ones) and is consistent with the observed absence of binding for such mutants. Interestingly, replacement with aspartic acid may be able to make a similar interaction, however the greater desolvation penalty of the charged side chain upon FcγR binding likely results in the reduced binding of this variant.

Finally, the intermolecular interaction between the aglycosylated S298G/T299A mutant and FcγRIIA includes a salt bridge formed between D265 on the B chain of the Fc dimer and K117 on the FcγR. In the wild-type structure, this interaction is shielded from solvent by the oligosaccharide chain. In the aglycosylated S298G/T299A mutant this salt bridge is exposed to the solvent, which nearly halves the screened electrostatic interaction energy compared to wild type (−5 kcal/mol vs. −10 kcal/mol). However, this effect is more than compensated in the S298G/T299A mutant by a reduced desolvation penalty (Lee and Tidor, *Protein Sci.* 10:362-377, 2001), a measure of the loss of electrostatic interactions with solvent upon binding, resulting in an overall stabilized structure. This effect is illustrated by a reduction in the residual electrostatic potential present on D265(B) in the mutant compared to the wild-type; similarly, the S298G mutation results in a reduced desolvation penalty that contributes to the stability of the mutant complex. Thus, the predictions made by this homology model provide a hypothetical mechanism for the stability of the aglycosylated Fc:FcγR complex, resulting from hydrogen bonding and electrostatic interactions altered in the aglycosylated mutant.

Aglycosylated Fc Variants that Bind hFcγRIIIA:

To evaluate the contribution of individual sidechains in the C′/E loop to FcγR engagement, as well as the nature of the specificity between FcγRIIA and FcγRIIIA seen in S298G/T299A, we constructed the full set of single point mutations at positions 297, 298, and 299, and assayed yeast-secreted IgG variants for binding to both FcγIIA and FcγIIIA (FIG. 4A-4E). Side chain scanning of 297 and 299 revealed additional mutations that remove the glycosylation motif but retain residual weak receptor binding: T299H to FcγIIA, and N297D and N297H to FcγIIIA$^{176V}$. T299A is the only aglycosylated mutant identified that displays dual specificity, exhibiting improved binding to FcγIIA while retaining moderate binding to the FcγIIIA$^{176V}$ allele. Interestingly, the nature of the sidechains at position 299, and not just glycosylation, greatly impacts receptor binding, as the yeast-expressed glycosylated T299S mutant binds all receptors to a much lesser extent than the wild-type Fc.

Figures 4A, 4B, 4C, 4D, 4E:
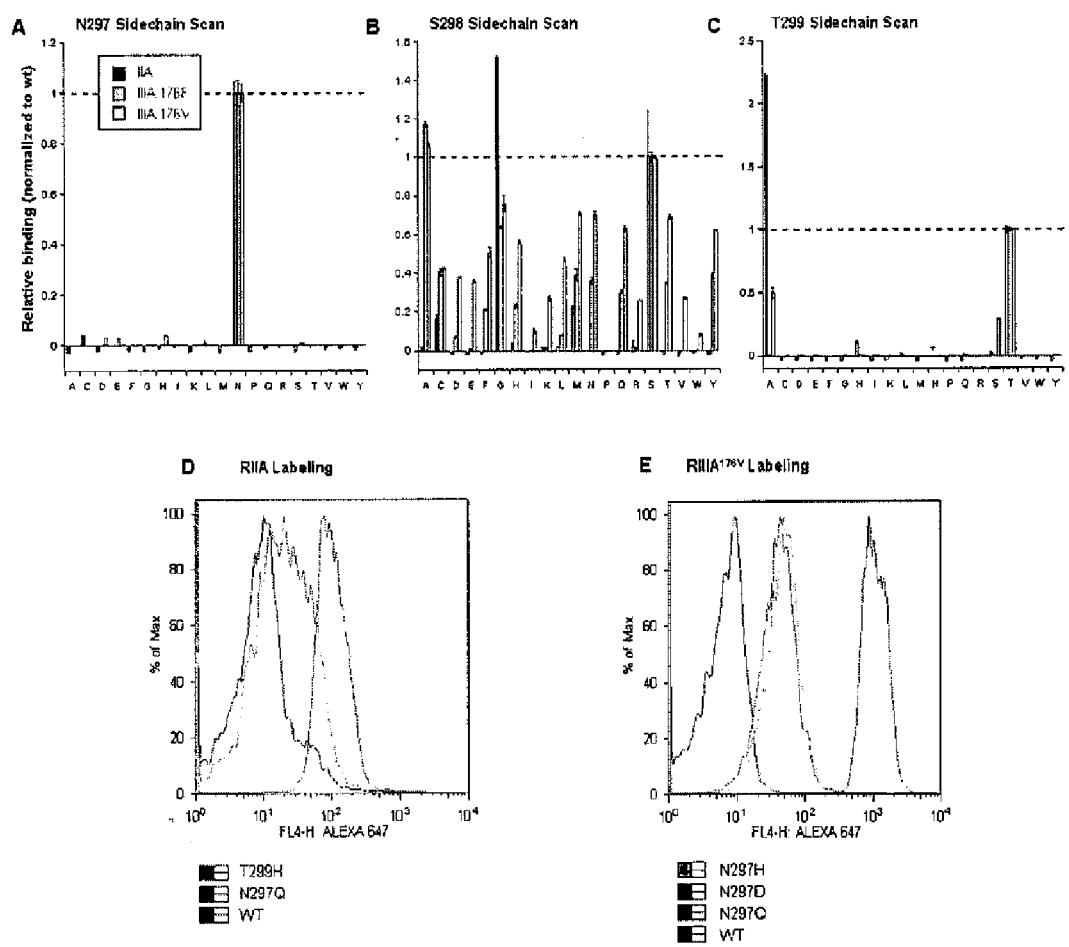
FIGS. 4A-4E depict the results of a sidechain scanning analysis of Fc positions 297, 298, and 299. The bar graphs of FIGS. 4A-4C resulted when yeast-secreted 4m5.3 hIgG1 point mutants were loaded on fluorescein-conjugated yeast and assayed for binding to 10 nM FcγRIIA131R, FcγRIIIA176V, and FcγRIIIA176F streptavidin-Alexa 647 tetramers by flow cytometry. All data represent the average of two trials and are normalized to the wild-type signal; * indicates binding to variant not determined: The histograms of FIGS. 4D and 4E depict FcγRIIA131R streptavidin-Alexa 647 and FcγRIIIA176V streptavidin-Alexa 647 tetramer labeling of weakly binding aglycosylated clones.

In contrast to positions 297 and 299, where mutations largely disrupt the N-linked glycosylation motif Asn-X-Ser/Thr, multiple substitutions in a glycosylated Fc background are tolerated at position 298 (FIG. 4B). FcγRIIA binding is much more sensitive to substitution at position 298, with only glycine (S298G) maintaining a level of binding that is comparable to wild type. In contrast, FcγRIIIA tolerates an array of substitutions at position 298, and the data highlight potential mutations for engineering FcγRIIIA vs. FcγRIIA/IIB specificity, such as the previously identified S298A and S298N mutations (Shields et al., *J. Biol. Chem.* 276:6591-6604, 2001; Stavenhagen et al., *Cancer Res.* 67:8882-8890, 2007). Only S298G maintained engagement to both FcγRIIA and FcγRIIIA in our assay, a finding that taken together with a preference for threonine at 299 (T299) suggests an explanation for the conservation of the motif N-S/G-T in IgG CH2 domains across virtually all species.

Figures 5A, 5B:
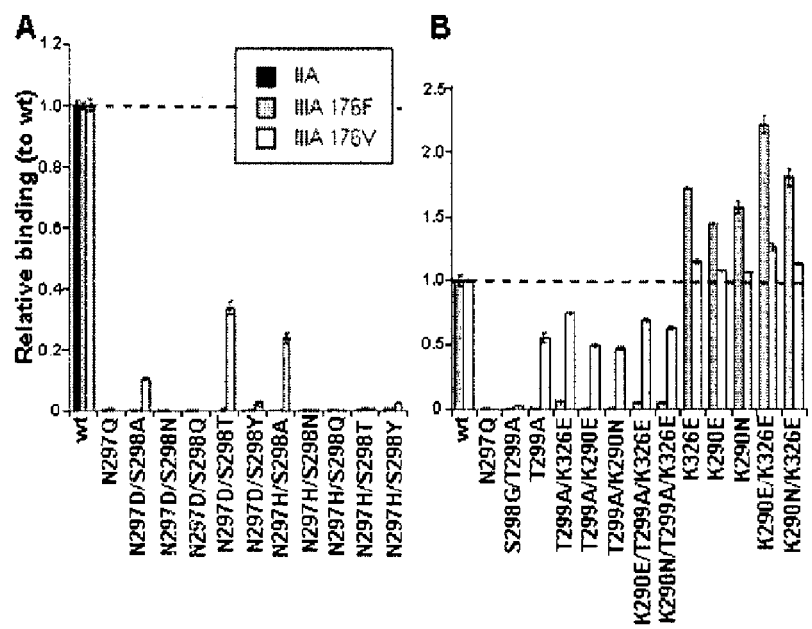
FIGS. 5A and 5B are bar graphs showing the results of tests to identify aglycosylated Fc mutants with FcγRIIIA binding activity. Yeast-secreted 4m5.3 hIgG1 C'/E loop double point mutants (A) or T299A point mutants with the 'second-site' mutations K326E and K290E/N (B) were loaded on fluorescein-conjugated yeast and assayed for binding to 10 nM FcγRIIIA176V, FcγRIIIA176F, and FcγRIIA131R (for A only) streptavidin-Alexa 647 tetramers by flow cytometry. All data represent the average of two trials and are normalized to the wild-type signal.

While our initial efforts focused on FcγRIIA resulted in specificity for FcγRIIA and FcγRIIB at the expense of FcγRIIIA binding, the sidechain scanning data suggested that aglycosylated Fcs that bind FcγRIIIA with comparable affinity to wild type could also be identified. Within the C′/E loop, rational design of double mutants based upon the weakly FcγRIIIA-binding N297D and N297H substitutions yielded variants that bound FcγRIIIA$^{176V}$ at levels 10 to 40% of wild type and with specificity for FcγRIIIA (FIG. 5A), a desired property in engineering Fcs with enhanced immune effector functions (Desjarlais et al., *Drug Discov. Today* 12:898-910, 2007). In a separate strategy, the consensus mutations K326E, K290E, and K290N—identified in a separate screen for improved FcγRIIA binding as well as through the efforts of previous groups (Stavenhagen et al., *Cancer Res.* 67:8882-8890, 2007; Idusogie et al., *J. Immunol.* 166:2571-2575, 2001)—were introduced into the T299A background. Incorporation of the K326E mutation, located at the base of the F/G loop, led to enhanced binding for FcγRIIA, approaching wild type levels for FcγRIIIA$^{176V}$ and weakly binding FcγRIIIA$^{176F}$ (FIG. 5B). This result suggests that additional second-site mutations at contact interfaces other than the C′/E loop can lead to aglycosylated FcγRIIIA- and FcγRIIA-binding Fcs with a range of affinities and specificities.

Until this study, the general knowledge of the binding interaction between IgG and FcγRs indicated a dependence on the N-linked glycan attached to asparagine 297 on the IgG heavy chain. The Fc variants described here clearly demonstrate that glycosylation is not a strict requirement for FcγR engagement, either in vitro or in vivo. In an initial strategy, by generating aglycosylated Fc variants that bind to FcγRIIA and FcγRIIB, we could demonstrate that the set of mutations necessary to switch from a wild-type glycosylated binder to a functionally aglycosylated binder is fairly small. In our case it involved the introduction of only two point mutations. In a second more directed screening strategy, we could further demonstrate that by introducing additional modifications into our aglycosylated mutants we can combine features from single mutants discovered from different screenings, thereby modulating the overall affinity features of the IgG variant. This combinatorial behavior of the contribution of single mutations is of special interest for the engineering of IgG variants with very well defined binding properties.

In addition to the enhanced FcγRIIA$^{131R}$ binding observed in the aglycosylated S298G/T299A variant, we were able to restore binding to FcγRIIIA$^{176V}$ to near wild-type levels, suggesting that further engineering can also lead to aglycosylated variants with wild-type or improved binding to FcγRIIIA. In particular, we anticipate that introducing mutations into the T299A background, which weakly binds both FcγRIIA and FcγRIIIA, will lead to fully FcγR competent aglycosylated antibody variants. Building upon these aglycosylated FcγRIIIA-binding variants will be essential for their potential use as cytotoxic antibodies, which have emerged as a promising class of therapeutics for treatment of human cancer in recent years (Waldmann, Curr. Opin. Immunol. 9:269-277, 2003). Support for a critical role for FcγR engagement in the mechanism of anti-tumor activity, and specifically for FcγRIIIA, has come from three independent studies which found a strong positive correlation between patient response and the presence of specific alleles of the activating FcγR FcγRIIIA that conferred enhanced binding for the IgG1 Fc domain of the antibody (Cartron et al., Blood 99:754-758, 2002; Weng et al., J. Clin. Oncol. 22:4717-4724, 2004; Weng and Levy, J. Clin. Oncol. 21:3940-3947, 2003). While the S298G/T299A variant does not bind complement, the above studies, as well as murine models that demonstrate a dominant role for FcγR engagement in therapeutic antibody activity (Nimmerjahn and Ravetch, Curr. Opin. Immunol. 19:239-245, 2007), suggest that restoration of complement binding would be unnecessary for engineered Fc variants. In addition to their ability to bind FcγR, it will also be important to assess the stability of these variants, as previously characterized Fc variants (Oganesyan et al., Mol. Immunol. 45:18 Mimura et al., Mol Immunol 37:697-706, 2000-1882, 2008) and deglycosylated wild-type Fc (Mimura et al., Mol Immunol 37:697-706, 2000) have displayed reduced thermal stability.

Figure 6:
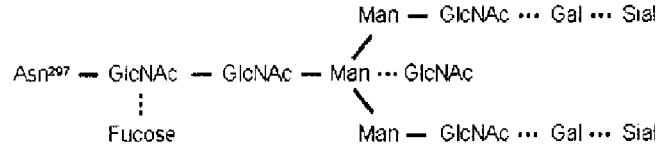
FIG. 6 is a representation of the N-linked glycan attached to Asn297. GlcNAc, N-acetylglucosamine; Man, mannose; Gal, galactose; Sial, sialic acid. Dark lines represent core glycosylation, dotted lines represent glycoforms variably attached to the core structure.

Given the small number of mutations required to achieve N-linked glycosylation-independent FcγR binding, it is striking that all naturally occurring IgGs utilize this post-translational modification nevertheless. Among different antibodies there is variation in the fucose and galactose-sialic acid attached to the core glycan structure (FIG. 6), and it has been reported that these variations dramatically influence the antibody activity. The absence of fucose in the glycan was reported to enhance the affinity of hFcγRIIIA for IgG up to 50-fold (Shields et al., J. Biol. Chem. 277:26733-26740, 2002) and thereby switch the antibody into an inflammatory mode. This is required, for example, for cytotoxic antibodies, but also occurs when autoantibodies generate pathogenic immune complexes and activate autoimmune cascades. In contrast to fucose, the presence of terminal sialic acid was demonstrated to be the critical factor for the anti-inflammatory action of high dose IVIG (Kaneko et al., Science 313:670-673, 2006; Anthony et al., Science 320:373-376, 2008). Sialic acid reduces the affinity of FcγRs to IgG by 5-10 fold (Kaneko et al., Science 313:670-673, 2006) and, in addition, marks IgGs and subsequently allows them to bind to non-FcR lectins (Anthony et al., Science 320:373-376, 2008) and mediate downstream actions through these novel interactions, resulting in anti-inflammatory responses, including the upregulation of FcγRIIB on effector macrophages (Nandakumar et al., Eur. J. Immunol. 37:2973-2982, 2007). The conservation of the N-S/G-T glycosylation motif among different species at the expense of this post-translational variability supports the view that the glycan, although not necessarily required for FcγR binding, serves as a platform for further modulation of the IgG's activity, enabling post-translational switching or tuning of the IgG function between an anti-inflammatory or inflammatory mode.

Finally, our demonstration that IgG variants can be generated that have uncoupled FcγR binding from N-linked glycosylation opens up new possibilities for protein engineering and biomanufacture. Our results suggest that receptor binding affinity and specificity can be engineered on the simpler template of an unmodified polypeptide chain, and these properties selected for by yeast surface display of aglycosylated Fc mutant libraries. Such mutants could then be produced in essentially any recombinant expression system without loss of the desired altered effector functions.

The following materials and methods were used in connection with the work described above.

Library Construction:

Libraries were constructed by homologous recombination of a mutated heavy chain constant region insert into the 4m5.3 heavy chain yeast secretion vector template according to previously published methods (Chao et al., Nat. Protoc. 1:755-768, 2006). The 4m5.3 heavy chain secretion vector was previously constructed from the pRS316 shuttle vector by insertion of the GAL10 promoter and alpha terminator, signal peptide, and 4m5.3 variable heavy chain domain upstream of the hIgG$_1$ CH1 to CH3 constant domains.

4m5.3 heavy chain template vector was prepared by digestion with NheI (New England Biolabs) and XhoI (New England Biolabs), which flank the 5' region of the hIgG$_1$ CH1 domain (NheI) and 3' region of the CH3 domain (XhoI). Saturation mutagenesis of the C'/E loop was performed by gene reconstruction with the oligonucleotides 297-299NNK (all oligos from Integrated DNA Technologies), 296-299NNK, and 297-300NNK for each of the three libraries, respectively. In a first PCR step, the mutagenic oligo and reverse primer 4m-CH3-epPCR-rev were used to amplify the region 5' of the C'/E loop through the 3' region of the CH3 domain, using the wild type vector as a template. In a second PCR step, this PCR product was used along with the forward primer 4m-CH1-epPCR-for to amplify the 3' region of the 4m5.3 variable heavy chain to the 3' end of the CH3 domain, reconstructing the heavy chain CH1 to CH3 gene insert with ~50 base pairs of overlap with the digested template vector for efficient yeast homologous recombination.

Gene inserts were transformed with digested template vector by electroporation into the yeast strain YVH10/LC, a derivative of the yeast strain YVH10, containing a chromosomally integrated copy of the 4m5.3 light chain yeast secretion vector. The 296-299 and 297-300 saturation libraries had ~$6 \times 10^7$ transformants, 60-fold greater than their theoretical diversity at the DNA level ($32^4$~$1.0 \times 10^6$); the 297-299 library had ~$4 \times 10^7$ transformants.

Oligonucleotides:

```
297-299NNK
                                        (SEQ ID NO: 1)
(5'-AGCCGCGGGAGGAGCAGTACNNKNNKNNKTACCGTGTGGTCAGC
GTCCT)

296-299NNK
                                        (SEQ ID NO: 2)
(5'-CAAAGCCGCGGGAGGAGCAGNNKNNKNNKNNKTACCGTGTGGTC
AGCGTCCT)

297-300NNK
                                        (SEQ ID NO: 3)
(5'-AGCCGCGGGAGGAGCAGTACNNKNNKNNKNNKCGTGTGGTCAGC
GTCCTCAC)

4m-CH1-epPCR-for
                                        (SEQ ID NO: 4)
(5'-ATGGAATACTTGGGTCAAGGAACCTCAGTCACCGTCTCCGCTAG
C)

4m-CH3-epPCR-rev
                                        (SEQ ID NO: 5)
(5'-ATTTTGTTACATCTACACTGTTGTTATCAGATTTCGCTCGAGTC
A)

297NNK
                                        (SEQ ID NO: 6)
(5'-CCGCGGGAGGAGCAGTACNNKAGCACGTACCGTGTGGTCAG)

298NNK
                                        (SEQ ID NO: 7)
(5'-GCGGGAGGAGCAGTACAACNNKACGTACCGTGTGGTCAGCG)

299NNK
                                        (SEQ ID NO: 8)
(5'-GGAGGAGCAGTACAACAGCNNKTACCGTGTGGTCAGCGTC)

297NHC
                                        (SEQ ID NO: 9)
(5'-CCGCGGGAGGAGCAGTACNHCAGCACGTACCGTGTGGTCAG)

298NHC
                                        (SEQ ID NO: 10)
(5'-GCGGGAGGAGCAGTACAACNHCACGTACCGTGTGGTCAGCG)

299NHC
                                        (SEQ ID NO: 11)
(5'-GGAGGAGCAGTACAACAGCNHCTACCGTGTGGTCAGCGTC)
```

N, H, and K encode the following groups of nucleotide bases: N encodes all four nucleotides; K encodes G and T; H encodes A, C, and T.

Library Screening:

Library screening was performed using the cell surface secretion assay (CeSSA) (Rakestraw et al., *Biotechnol. Prog.* 22:1200-1208, 2006). Briefly, libraries were grown in SD-CAA (2% glucose, 0.67% yeast nitrogen base, 0.54% $Na_2HPO_4$, 0.86% $NaH_2PO_4 \cdot H_2O$, 0.5% casein amino acids) at 30° C. to an $OD_{600}$ of ~5, and then induced in YPG (2% galactose, 2% peptone, 1% yeast extract, 0.54% $Na_2HPO_4$, 0.86% $NaH_2PO_4 \cdot H_2O$) for 12 hrs at 20° C. Following this pre-induction phase, yeast were labeled with fluorescein-PEG-NHS (Nektar) and re-induced in YPG containing 15% PEG (w/v) at 20° C. for 36 hrs. Cells were washed with PBS containing 0.1% (w/v) BSA (PBS/BSA) and labeled with biotinylated hFcγRIIA$^{131R}$ preloaded onto streptavidin-Alexa 647 (Invitrogen). The library was sorted on a BD FACSAria (Becton Dickinson) and collected cells grown in SD-CAA supplemented with penicillin/streptomycin (Invitrogen), for a total of three rounds of screening. Library populations were labeled at increasingly stringent concentrations of FcγRIIA tetramer as follows: round one (50 nM FcγRIIA tetramer), round two (2 nM FcγRIIA tetramer), and round three (80 pM FcγRIIA tetramer). All clones isolated from screening were re-transformed into YVH10/LC and individually assayed for FcγRIIA binding.

Site Directed Mutagenesis:

For sidechain scanning of positions 297, 298, and 299, mutagenesis of the 4m5.3 heavy chain yeast secretion vector was performed using the Quikchange Multi Site-Directed Mutagenesis Kit (Stratagene) and the degenerate oligos 297NNK, 298NNK, 299NNK, 297NHC, 298NHC, and 299NHC. Clones were identified and confirmed by subsequent sequencing and re-sequencing. All other point mutants were constructed by PCR-amplification of the entire vector using complementary primers containing the desired point mutations.

Characterization of Yeast-Secreted Fc Mutants:

Fc mutants freshly transformed into YVH10/LC were grown in 5 ml SD-CAA at 30° C. until an $OD_{600}$~5, then induced in 5 ml YPG at 20° C. for 72 hrs. Cell culture supernatants were loaded onto fluorescein-conjugated yeast overnight at 4° C.; yeast were then washed with PBS/BSA, labeled with 10 nM of biotinylated FcγR preloaded onto streptavidin-Alexa 647 at 4° C. for >2 hrs, and analyzed by flow cytometry. Labeling with 10 µg/ml Protein A-Alexa 647 (Invitrogen) was performed as a separate IgG loading control for all samples.

Mice:

$\gamma^{-/-}$ FcγRIIB$^{-/-}$ mice were generated, backcrossed for 12 generations to the C57BL/6 background and crossed to hFcγRIIA$^{tg}$ mice (The Jackson Laboratory, Bar Harbor, Me.). Female mice at 2 to 4 months of age were used for the experiments and maintained at the Rockefeller University animal facility. All experiments were performed in compliance with federal laws and institutional guidelines and have been approved by the Rockefeller University (New York).

Cell Culture:

CHO cells were cultured according to the ATCC guidelines. CHO-hFcγRIIA$^{131H}$, CHO-hFcγRIIA$^{131R}$ and hFcγRIIB were obtained by transfection of the pCMV-Script-hFcγRIIA$^{131H}$, CHO-hFcγRIIA$^{131R}$ and hFcγRIIB plasmids and subsequent selection with 1 mg/ml geneticin (Invitrogen).

Antibodies and Recombinant Proteins:

The 6A6-human Fc chimeric variants and soluble hFcγ-receptors were produced by transient transfection of 293T cells and subsequent purification from culture supernatants. For protein production, cells were cultured in DMEM medium supplemented with 1% Nutridoma SP (Roche). Cell culture supernatants were harvested 6 days after transfection, and protein was precipitated by ammonium sulfate precipitation. The 4m5.3-human Fc chimeric variants were produced by transient transfection of 293F cells (Invitrogen) and subsequent purification from cell culture supernatants. For protein production, cells were cultured in Freestyle 293F Expression Medium (Invitrogen). Recombinant receptors were purified with Ni-NTA (Qiagen) and recombinant antibodies were purified with protein G sepharose (GE Healthcare) or immobilized protein A (Pierce) by affinity chromatography. All proteins were dialyzed against PBS. Purity was assessed by SDS-PAGE followed by Coomassie Blue staining.

Immune Complex Binding Assay:

For studying immune complex binding to surface FcγRs, ICs were generated by incubating 10 µg of the respective 4m5.3 (anti-FITC) chimera with 10 µg of BSA-FITC (Sigma) in 1 ml PBS for 2 hours at 37° C. while shaking gently. CHO cells were stained for 2 hours at 4° C. with 1 µg, 0.5 µg, 0.2 µg or 0.1 µg of ICs, washed with PBS and analyzed by FACS analysis.

Surface Plasmon Resonance Analysis:

To determine the interaction between soluble hFcγ-receptors RIa (R&D Systems), RIIA$^{131H}$, RIIA$^{131R}$, RIIB, RIIIA, C1q (Calbiochem) and 4m5.3 antibody chimera, steady state affinity measurements on a Biacore T100 biosensor were performed. Antibodies were immobilized at high densities to CM5 sensor chips (Biacore) by standard amine coupling. Soluble hFcγ-receptors were injected in 5 different concentrations through flow cells at room temperature in HBS-EP running buffer (Biacore) for 3 min at a flow rate of 30 µl/min and dissociation was observed for 10 min. $K_d$ values were calculated after subtraction of background binding to a control flow cell using Biacore T100 Evaluation software.

Lectin Blot:

10 µg of 4m5.3 wt, N297Q, and S298G/T299A antibody chimera were resolved by SDS-PAGE using a polyacrylamide gel (NuPAGE, Invitrogen) under non-reducing conditions. Proteins were transferred to a polyvinylidene difluoride (PVDF) membrane (Millipore), blocked with Western Blocking Reagent (Roche), and followed by incubation with biotinylated LCA lectin (2 µg/ml, Vector Laboratories) and alkaline phosphatase-conjugated goat anti-biotin antibody (Sigma). Bound antibody was visualized with 4-nitro blue tetrazolium chloride/5-bromo-4-chloro-3-indolyl phosphate (Roche).

In Vivo Model Systems:

Mice were injected intravenously with 50 µg 6A6-hFc1 wt, N297A, or S298G/T299A in 100 µl PBS. Platelet counts were determined before injection and at 4, 24, and 72 hours after injection by blood collection of 50 µl from the retro-orbital plexus and measuring platelet counts of a 1:10 dilution in PBS/5% BSA in an Advia 120 hematology system (Bayer). Platelet clearance for mice treated with each 6A6-hIgG$_1$ variant was analyzed 4 h post-injection by a one-way ANOVA test using SIGMASTAT. Error bars represent the standard deviation of three mice per group.

Computational Modeling:

Beginning from the crystal structure of the extracellular portion of the Fcγ-RIIIB receptor bound to the Fc region of the human IgG$_1$ immunoglobulin (PDB ID 1E4K) (Sondermann et at, *Nature* 406:267-273, 2000), structures were prepared using methods from Lippow et al. (Lippow et al., *Nat. Biotechnol.* 25:1171-1176, 2007). Hydrogen atoms were placed and the sidechains of H116(C) and H131(C) on the receptor were flipped by 180° around $\chi_2$ and treated in their neutral, ε-protonated form. In the Fc fragment, all histidine sidechains were neutral and protonated as indicated, to maximize hydrogen bonding potential: 268(A)-δ, 268(B)-ε, 285(A)-δ, 285(B)-δ, 310(A)-δ, 310(B)-ε, 429(A)-δ, 429(B)-δ, 433(A)-δ, 433(B)-δ, 435(A)-δ, and 435(B)-δ. A preliminary homology model of the corresponding FcγRIIA complex was constructed on this backbone as follows. All non-alanine, non-glycine residues further than 4.75 Å from an interface residue were replaced by alanine. Both glycosylated and aglycosylated forms of the structure were prepared, and in the glycosylated structure, a sliding, restrained harmonic minimization was performed on the sidechain of the N-glycosylated N297(B). Partial atomic charges for the N-glycosylated N297(C) residues were derived by fitting to the electrostatic potential using the restrained fitting methods of Bayly et al. (Bayly et al., *J. Physical Chem.* 97:10269-10280, 1993) for each monosaccharide. The charges associated with hydrogens missing in the polysaccharide were added to their parent atoms to ensure charge conservation. To generate the FcγRIIA receptor structure, all FcγRIIIB interfacial residues were mutated to their FcγRIIA$^{R131}$ counterparts using the dead-end elimination and A* protocol described by Lippow et al. (Lippow et al., *Nat. Biotechnol.* 25:1171-1176, 2007) in the presence of wild-type or mutant Fc region. For each mutant sequence, the global minimum energy conformation, as well as a collection of progressively higher energy conformations, was identified in the context of discrete rotameric conformational freedom of all placed sidechains except the glycosylated form of N297. All of the Fc mutants examined were generated in the presence of the receptor during this conformational search. Note that one interfacial residue in the linker region of the Fcγ structure (E86 in the FcγRIIA sequence) was left as a glycine, as all glutamate rotamers searched had a van der Waals clash with the receptor backbone. In the unbound FcγRIIA crystal structure (Maxwell at al., *Nat. Struct. Biol.* 6:437-442, 1999), the two domains of the receptor separate slightly to accommodate this larger residue. The solvent screened electrostatic interactions and the residual electrostatic potential upon binding for these structural models were computed by solving the linearized Poisson-Boltzmann equation as described by Lee and Tidor (Lee and Tidor, *Protein Sci.* 10:362-377, 2001). PARSE radii and charges were used for all examined complexes (Sitkoff at al., *J. Physical Chem.* 98: 1978-1988, 1994).

Example 2

Engineering Aglycosylated Fc Variants with FcγRIIIA Binding

As described above, our initial screening methodology focused on engineering the Fc C'/E loop, which contains the N-linked glycosylation site (Asn$^{297}$-Ser$^{298}$-Thr$^{299}$) and makes direct contacts with FcγR. A library screen of all possible C'/E loop variants yielded a variant (S298G/T299A) that binds FcγRIIA and FcγRIIB with approximately wild-type affinity, but does not bind FcγRIIIA with wild-type affinity. A second approach, based on screening each single point mutation within the C'/E loop, then combining candidate mutations, identified variants that weakly bind FcγRIIIA$^{176V}$—T299A, N297D, N297H, and the double mutants N297D/S298T, N297D/S298A, and N297H/S298A—demonstrating that aglycosylated Fc regions can engage this FcγR as well. However, given the importance of FcγRIIIA to therapeutic outcome, these variants may not have optimum therapeutic utility.

We have found aglycosylated hIgG$_1$ variants that can engage all of the low-affinity hFcγRs with wild-type or improved binding affinity, thus identifying variants that might effectively substitute for the wild-type, glycosylated hIgG$_1$. In doing so, we have focused on engineering additional loops of the Fc domain that make contact with FcγR, screening libraries that encode all possible amino acid diversity within segments of these loops to enrich variants with improved FcγRIIIA$^{176F}$ binding. Such variants, when placed in the previously identified aglycosylated backgrounds that allow for weak FcγRIIIA$^{176V}$ binding, yield fully FcγR competent aglyco Fc's with a range of affinities. In addition, we find that our approach of searching sequence space at contact loops in a focused manner, which allows us to screen all possible amino acid diversity at these sites in short segments, uncovered variants with mutations that act cooperatively, and thus are not easily predicted by combining the properties of single point mutations.

Engineering Approach and Screening Methodology:

Previously, we showed that the binding affinity of aglycosylated Fc regions can be modulated by placing 'second-site' mutations selected for improved binding to FcγRs in a glycosylated background into an aglycosylated background. Here, combining a mutation located near a contact interface (K326E) with the mutation T299A improved FcγRIIIA binding relative to T299A alone, while second-site mutations at a site distant from the contact interface (K290E/N) had no effect upon aglycosylated Fc binding. This result suggested that modulating the interactions about the Fc contact loops with FcγR, in a glycosylated background, could likewise translate into improved binding affinity in an aglycosylated background. To accomplish this, we set out to systematically ask what combinations of mutations at Fc contact loops yield improved FcγRIIIA binding.

Here, we constructed saturation libraries about three contact sites within the Fc—the lower hinge, the B/C loop, and F/G loop (FIGS. 7A and 7B)—and screened them by displaying these full-length hIgG$_1$ variants on the surface of yeast. In this display system, the femtomolar affinity scFv 4m5.3 (Boder et al., *Proc. Natl. Acad. Sci. USA* 97:10701-10705, 2000) has been reformatted as a hIgG$_1$, allowing 4m5.3 hIgG$_1$ Fc library variants to be captured on fluorescein-labeled yeast from which they are secreted by adapting features of a cell surface secretion capture assay (Rakestraw et al., *Biotechnol. Prog.* 22, 22:1200-1208, 2006) and the improved secretion of full-length hIgG$_1$ from *S. cerevisiae*. Contact interface libraries were constructed by fully-randomizing four amino acid stretches using degenerate NNK codons (N=ATCG, K=GT), which encode all 20 possible amino acids in 32 codons. This design approach allows for over-sampling the codon diversity ($32^4 \sim 1 \times 10^6$), and thus amino acid diversity, in these yeast-based libraries, which often have a transformation efficiency on the order of $1 \times 10^7$. The following libraries were constructed and pooled by contact region: lower hinge (234-237, 236-239), B/C loop (265-268, 267-270), and F/G loop (326-329, 327-330, 329-332, 331-334). As a target we chose the FcγRIIIA$^{176F}$ allele, which, given its weaker binding for wild-type Fc, likely represents a more stringent, as well as therapeutically relevant, barrier for improved FcγRIIIA binding. Pooled libraries were individually screened by two rounds of enrichment on FcγRIIIA$^{176F}$ coated magnetic beads followed by three rounds of fluorescence activated cell sorting (FACS) at increasing stringency.

B/C and F/G Loop Variants Enriched from Screen:

The sequences of variants enriched for FcγRIIIA$^{176F}$ binding after the second and third rounds of FACS (rounds four and five in total) for the B/C and F/G loop libraries are shown in FIGS. 8A-8D. Enrichment of only wild-type clones was observed from the lower hinge libraries. Clones enriched from the B/C loop libraries (FIGS. 8A and 8B) show an absolute preference for D265, consistent with the importance of this residue in binding FcγR (Shields et al., *J. Biol. Chem.* 276:6591-6604, 2001; Baudino et al., *J. Immunol.* 181:6664-6669, 2008). The majority of clones enriched from the screen have substitutions at positions 266-268, indicating that variation within the 265-268 sub-library more strongly contributed to FcγRIIIA$^{176F}$ binding. Enriched variants show a strong preference for mutation of H268 to Glu, and to a lesser extent a likewise negatively charged Asp. At position 266 there is a strong preference for either Leu or the wild-type Val, while position 267 appears to be more promiscuous to substitution, with enrichment of the wild type Ser, as well as more frequently Ala, Glu, and Asp. Of the clones enriched from the 267-270 sub-library (i.e. those clones with mutations at positions 269 and/or 270), there is a strong preference for retaining negative charge at E269 and D270, either as the wild-type residue or as E269D or D270E.

Clones enriched from the F/G loop libraries (FIGS. 8C and 8D) fall into two broad classes of loop diversity—those enriched from the 326-329 library and those with substitutions at the opposite end of the loop, primarily at position 332 and to a lesser extent at 334, both of which have been previously identified as modulating FcγRIIIA binding affinity (Shields et al., *J. Biol. Chem.* 276:6591-6604, 2001; Stavenhagen et al., *Cancer Res.* 67:8882-8890, 2007; Lazar et al., *Proc. Natl. Acad. Sci. USA* 103:4005-4010, 2006). Substitution of I332 with Glu dominates the screen, and has been previously shown to greatly enhance binding to all FcγRs, including FcγRIIIA$^{176V}$ and FcγRIIIA$^{176F}$ (Lazar et al., *Proc. Natl. Acad. Sci. USA* 103:4005-4010, 2006). Virtually all clones potentially enriched from the 331-334 sub-library (i.e. those with mutations at positions 333 and/or 334, or those lacking mutations at positions 329 and 330 found in the 329-332 sub-library) also contain a substitution at position 334, with a preference for Val and Ala, and to a lesser extent Ser, Glu, and Gln. These data are consistent with previous studies, in which K334A, K334E, K334Q, and K334V were shown to strengthen binding FcγRIIIA (Shields et al., *J. Biol. Chem.* 276:6591-6604, 2001), and the frequent enrichment of K334E and K334N from a random mutagenesis library for improved binding to FcγRIIIA (Stavenhagen et al., *Cancer Res.* 67:8882-8890, 2007).

Within the clones enriched from the 331-334 sub-library there is a strong preference for either the wild-type Pro at position 331 or Ser or Ala. P331A alone has been shown to have no effect on FcγRIIIA$^{176V}$ binding affinity, and P331S alone to reduce FcγRIIIA$^{176V}$ binding (Shields et al., *J. Biol. Chem.* 276:6591-6604, 2001). Interestingly, when P331 is mutated, it is almost always derived from the 331-334 sub-library and not the 329-332 sub-library, suggesting that the context of flanking residues is important to binding. Clones enriched from the 329-332 sub-library have a strong preference for substitution at position 330, and thus mutation of the wild-type Pro at position 331, within the background of I332E and A330x may be disfavored. Previous studies have shown that A330V alone slightly improves FcγRIIIA$^{176F}$ binding (Stavenhagen et al., *Cancer Res.* 67:8882-8890, 2007) and A330L in the context of I332E imparts improved FcγRIIIA$^{176F}$ binding (Lazar et at, *Proc. Natl. Acad. Sci. USA* 103:4005-4010, 2006).

In contrast, relatively little is known about how diversity at positions 326-328, and in particular position 327 and 328, impact FcγR binding. The variants enriched for FcγRIIIA$^{176F}$ from our screen from the 326-329 sub-library show a strong preference for substitution of K326 with the hydrophobes Ile, Leu, and Val. K326A has previously been shown to increase binding to all FcγRs (Shields et al., *J. Biol. Chem.* 276:6591-6604, 2001), while K326E, and to a lesser extent K326I and K326Q, were frequently enriched in a screen for improved binding to FcγRIIIA$^{176V}$ (Stavenhagen et al., *Cancer Res.* 67:8882-8890, 2007). In addition, multiple substitutions at position 326 impart improved binding to the complement component C1q (Idusogie et al., *J. Immunol.* 166:2571-2575, 2001). In our screen, A327 has a strong preference for Asp, although tolerates additional residues as well, with the similarly negatively charged Glu, the wild-type Ala, and Gly appearing multiple times; similarly, L328 has a strong preference for Ala and appears to tolerate multiple substitutions, with Gly appearing multiple times. Within the clones enriched from this sub-library, P329 is absolutely conserved, consistent with its substitution being disfavored within the 329-332 library. P329A alone has been shown to reduce binding to all FcγRs (Shields et al., *J. Biol. Chem.* 276:6591-6604, 2001).

Figures 8A, 8B, 8C, 8D, 9A, 9B:
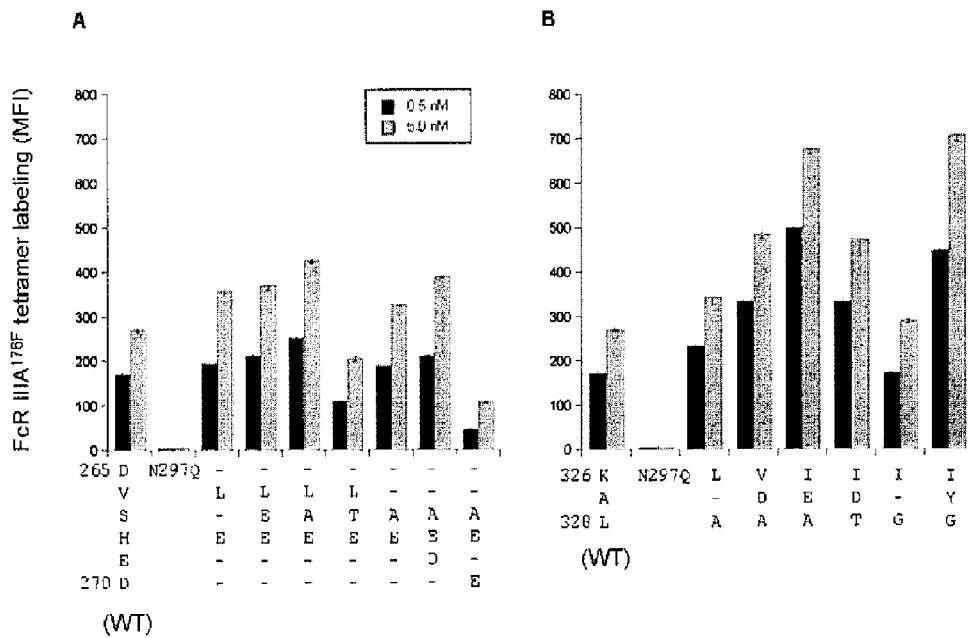
FIGS. 8A-8D are representations of the sequences of B/C and F/G loop variants enriched from an FcγRIIIA$^{176F}$ binding screen. Sequences of B/C loop clones enriched after the fourth and fifth rounds of screening are shown in FIGS. 8A and 8B, respectively. Sequences of F/G loop clones enriched after the fourth and fifth rounds of screening are shown in FIGS. 8C and 8D, respectively. Dashes represent the same residue as the wild-type sequence. Numbers in parenthesis represent the number of times a particular clone was present in the population sequenced.
FIGS. 9A and 9B are bar graphs illustrating the relative binding of various clones enriched from the screen. B/C loop (FIG. 9A) and F/G loop (FIG. 9B) 4m5.3 Fc variants enriched for improved FcγRIIIA176F binding from the yeast-based screen were expressed from HEK cells and assayed for relative binding to FcγRIIIA176F compared to wild-type (WT). Fluorescein-labeled yeast were incubated with cell culture supernatants, then labeled with either 0.5 nM or 5.0 nM of streptavidin Alexa 647 FcγR tetramer, and then cells analyzed by flow cytometry. Data represent the average of two trials, normalized by the relative IgG surface loading of a given variant compared to wild-type, as determined by a separate Protein A 647 loading control. Dashes represent the same residue as the wild-type sequence.

Binding of HEK Secreted B/C and F/G Loop Clones:

To determine whether variants enriched from this yeast-based screen impart improved FcγRIIIA binding when expressed from a more standard host, a subset of variants were subcloned into mammalian expression vectors, secreted from HEK cells, and assayed for their relative ability to bind FcγRIIIA$^{176F}$. Most B/C loop variants tested displayed a slight increase in binding affinity to FcγRIIIA$^{176F}$ compared to wild-type Fc (FIG. 9A). Within the S267A/H268E background, there is a slight preference for Leu at position 266 compared to the wild-type Val at position 266, suggesting that either of these residues can mediate FcγRIIIA$^{176F}$ binding. Within the V266L/H268E background, there is a slight preference for Ala or Asp over the wild-type Ser, although substitution to Thr results in a variant with reduced FcγRIIIA$^{176F}$ binding. Interestingly, the addition of D270E in the S267A/H268E background results in decreased binding to FcγRIIIA. The D270E mutation alone has been shown to impart slightly improved binding to FcγRIIIA but weakened binding to FcγRIIA$^{131R}$ and FcγRIIB (Shields et al., *J. Biol. Chem.* 276: 6591-6604, 2001; Stavenhagen et al., *Cancer Res.* 67:8882-8890, 2007), FcγRs with Arg at position 131 of the receptor, suggesting that multiple mutations within this loop may not act in an additive fashion.

Since the consensus mutations from our screen at positions I332 and K334 have been extensively characterized, we chose to look in more depth at the contributions of positions 326, 327, and 328 of the Fc to FcγRIIIA binding (FIG. 9B). As a whole, these F/G loop variants bind FcγRIIIA$^{176F}$ to a greater extent than the sampled B/C loop variants, with two F/G loop variants, K326I/A327Y/L328G (IYG) and K326I/A327E/L328E (IEA), binding FcγRIIIA$^{176F}$ to a much greater extent than wild-type. Interestingly, the presence of a Tyr at position 327 in the K326I/L328G background imparts a large increase in binding affinity, as K326I/L328G alone binds at near wild-type levels.

Figure 10:
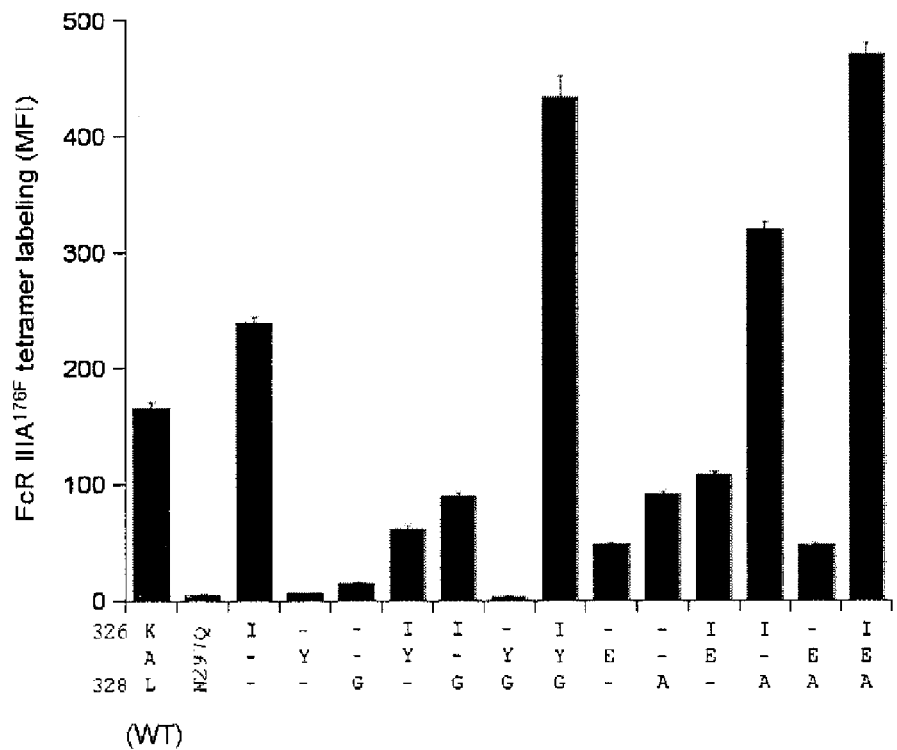
FIG. 10 is a bar graph depicting the results of mutational analysis of IYG and IEA variants. 4m5.3 Fc variants, comprising the ensemble of mutations present in the K326I/A327Y/L328G (IYG) and K326I/A327E/L328A (IEA) variants, were assayed for binding to FcγRIIIA176F. Fluorescein-labeled yeast were incubated with cell culture supernatants, then labeled with 5 nM of streptavidin Alexa 647 FcγR tetramer, and then cells analyzed by flow cytometry. Data represent the average of two trials, normalized by the relative IgG surface loading of a given variant compared to wild-type, as determined by a separate Protein A 647 loading control. Dashes represent the same residue as the wild-type sequence.

To assess the contribution of the individual mutations within these clones, as well as ask whether additional improved variants exists (such as those that could be present if, for example 10-fold more clones were sequenced and analyzed), we performed a detailed point mutant analysis of both the IYG and IEA variants (FIG. 10). K326I alone imparts an increase in binding affinity to FcγRIIIA$^{176F}$, suggesting that part of the large increase in binding affinity of the IYG and IEA variants compared to wild-type is due to the presence of this mutation. Interestingly, no other combination of mutations other than the triple mutant imparts improved binding in the IYG variant (and in most cases dramatically weakened binding), suggesting that for this variant substitution at A327 and L328, in the K326I background, act cooperatively to impart improved receptor binding. Similarly, substitutions at A327 and L328 in the IEA variant also act in a coordinated way with K326I. L328A by itself weakens receptor binding, but when placed alongside K326I results in a double mutant with strengthened binding compared to K326I alone. Likewise, A327E alone and A327E/K328A weaken receptor binding, yet in the context of the IEA variant yield substantially improved FcγRIIIA$^{176F}$ binding.

Figure 11:
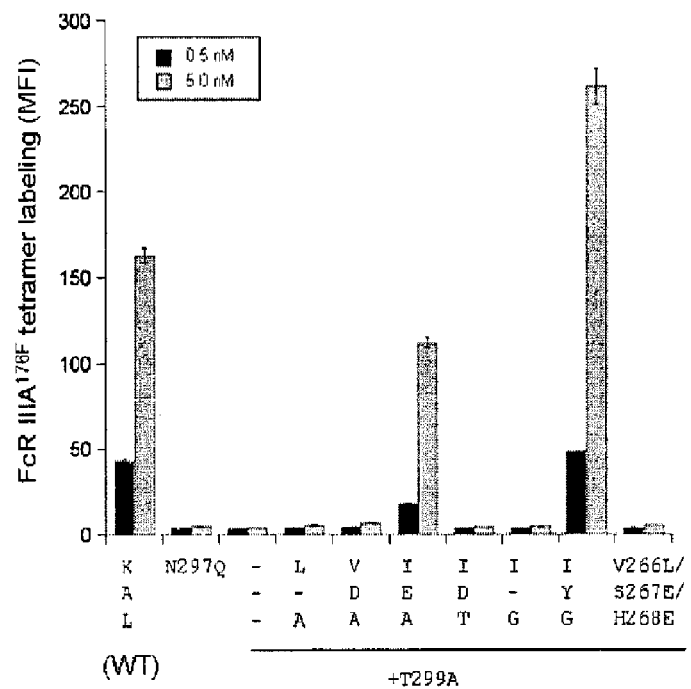
FIG. 11 is a bar graph depicting FcγRIIIA binding of aglycosylated F/G loop variants. Aglycosylated variants of the F/G loop clones enriched for improved FcγRIIIA176F binding and the most frequently enriched B/C loop clone (V266L/S267E/H268E) were assayed for binding to FcγRIIIA176F. The T299A mutation, which confers weak aglycosylated binding to FcγRIIIA 176V, was introduced into all clones. Fluorescein-labeled yeast were incubated with cell culture supernatants, then labeled with either 0.5 nM or 5.0 nM of streptavidin Alexa 647 FcγR tetramer, and then cells analyzed by flow cytometry. Data represent the average of two trials, normalized by the relative IgG surface loading of a given variant compared to wild-type, as determined by a separate Protein A 647 loading control. Dashes represent the same residue as the wild-type sequence.
Figures 12A, 12B, 12C, 12D:
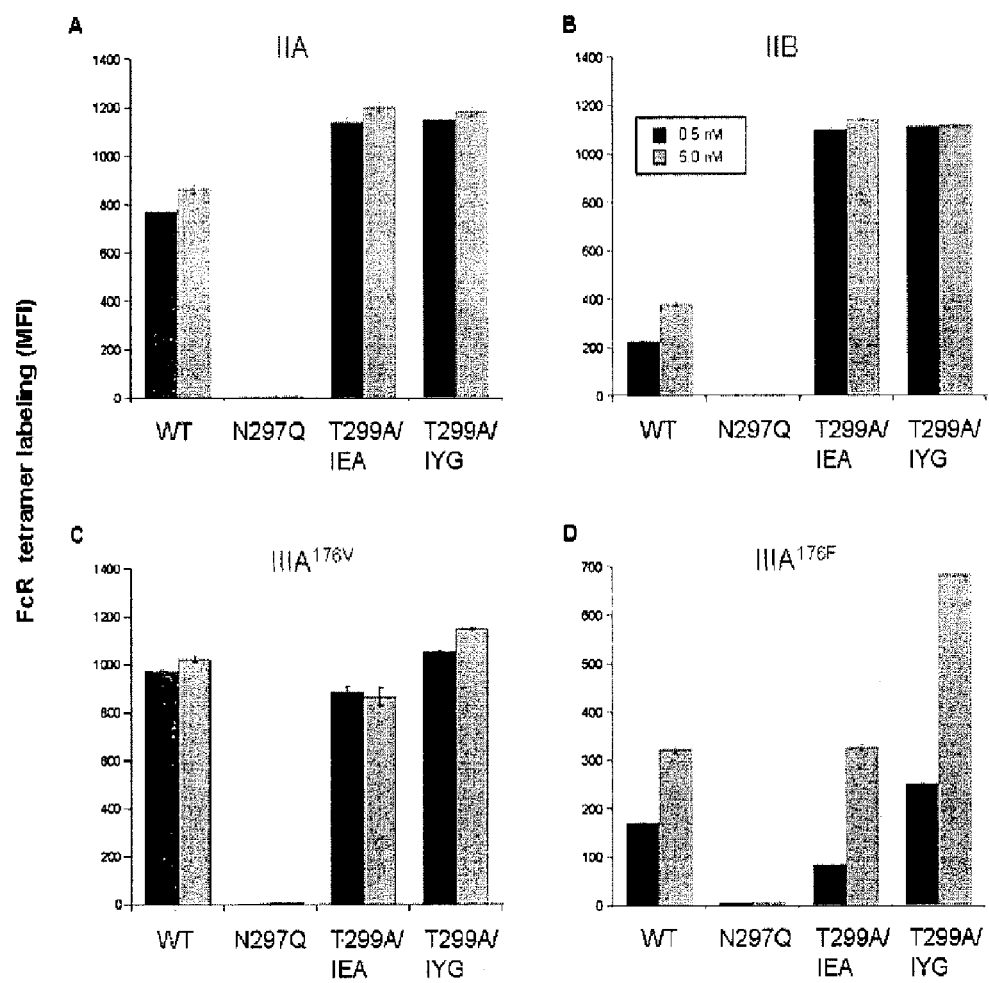
FIGS. 12A-12D are bar graphs depicting FcγR binding of T299A/IEA and T299A/IYG variants. T299A/IEA and T299A/IYG were assayed for relative binding to the panel of human FcγRs: FcγRIIA131R (FIG. 12A), FcγRIIB (FIG. 12B), FcγRIIIA176V (FIG. 12C), and FcγRIIIA176F (FIG. 12D). Fluorescein-labeled yeast were incubated with cell culture supernatants, then labeled with either 0.5 nM or 5.0 nM of streptavidin Alexa 647 FcγR tetramer, and then cells analyzed by flow cytometry. Data represent the average of two trials, normalized by the relative IgG surface loading of a given variant compared to wild-type, as determined by a separate Protein A 647 loading control.

Binding of Aglycosylated F/G Loop Variants:

To assess whether enriched variants from our screens could lead to aglycosylated Fc regions with improved FcγRIIIA binding, the T299A mutation was placed in the F/G loop variants described above, secreted from HEK cells, and as a stringent test of binding affinity, assayed for their ability to bind FcγRIIIA$^{176F}$ (FIG. 11). Only T299A/K326I/A327Y/L328G (T299A/IYG) and T299A/K326I/A327E/L328E (T299A/IEA) bound FcγRIIIA$^{176F}$ with detectable affinity, consistent with these mutations imparting the largest improvements in binding affinity in the glycosylated background. In this assay, T299A/IYG binds FcγRIIIA$^{176F}$ to a slightly greater degree than wild type hIgG$_1$, and T299A/IEA to a slightly lesser degree. In addition, both of these aglycosylated variants bind FcγRIIIA$^{176V}$, FcγRIIA$^{131R}$, and FcγRIIB at approximately wild-type or improved levels (FIGS. 12A-12D), demonstrating not only that aglycosylated Fc variants can be engineered that bind FcγRIIIA, but that such variants can be engineered to bind the panel of human low-affinity FcγRs as well. In particular, the binding to FcγRIIB (FIG. 12B) appears to be greatly strengthened compared to wild-type Fc for the T299A/IYG and T299A/IEA variants, and given the high sequence identity between receptors, likely greatly strengthened for FcγRIIA (FIG. 12A) as well (the similar signals in this panel likely represent saturation of binding, as there is little reduction in signal with a 10-fold decrease in receptor labeling concentration).

Modulating FcγRIIA and FcγRIIB Binding of Aglycosylated FcγRIIIA-Binding Variants:

Given the large increase in binding to FcγRIIA and FcγRIIB binding imparted by using the T299A mutation to place the F/G loop variants in an aglycosylated background, we next sought to reduce the binding of the aglycosylated variant Fcs to these two receptors by placing the K326I/A327Y/L327G ("IYG") F/G loop variant in alternative aglycosylated C'/E loop backgrounds. Previously, we identified the double mutants N297D/S298T ("DTT"), N297D/S298A ("DAT"), and N297H/S298A ("HAT") as imparting weak aglycosylated binding to FcγRIIIA$^{176V}$, but no detectable binding to FcγRIIA$^{131R}$, suggesting that these variants preferentially bind FcγRIIIA. As expected, the variants T299A/IYG, DTT/IYG, DAT/IYG, and HAT/IYG all display varied FcγR-binding profiles, with the DTT/IYG, DAT/IYG, and HAT/IYG variants having greatly reducing FcγRIIA and FcγRIIB binding compared to T299A/IYG. All variants appear to bind the FcγRIIIA$^{176V}$ allele equally as well as wild-type Fc, and most (DTT/IYG, T299A/IYG, and DAT/IYG) display similar, if not slightly improved binding for the FcγRIIIA$^{176F}$ allele. Interestingly, HAT/IYG has greatly reduced binding for both FcγRIIA and FcγRIIB, and is essentially FcγRIIIA specific. The DTT/IYG and DAT/IYG variants come closest, in this assay, to displaying near wild-type binding for all low affinity FcγRs-DAT/IYG has similar binding as wild-type Fc for FcγRIIA and increased binding for FcγRIIB; DTT/IYG has reduced binding for FcγRIIA and similar binding as wild-type for FcγRIIB. Taken together with the T299A/IYG variant, these variants clearly demonstrate that aglycosylated IgG variants can be engineered to bind all of the low-affinity FcγRs, and with a range of affinities and specificities.

In the present study, we demonstrate that aglycosylated IgG variants can be engineered to engage FcγRIIIA at wild-type or improved levels, and that these variants can bind to all of the human low-affinity FcγRs at wild-type or improved levels. Such variants represent a further step towards the development of fully-functional aglycosylated IgGs and the production of therapeutic antibodies in virtually any expression system without regard to post-translational processing.

In engineering these aglycosylated variants, we chose a modular design strategy, based upon the hypothesis that properties imparted by altered contact loops will be additive. By combining the mutant aglycosylated C'/E loops described above with an altered F/G loop isolated for improved FcγRIIIA[176F] binding, we have generated a series of aglycosylated Fc variants capable of binding FcγRIIIA whose relative receptor binding properties mirror those of the C'/E loop variants alone.

In addition, in screening for variants with improved FcγRIIIA binding, we chose a directed evolution approach that allowed us to experimentally explore the sequence space at the sites of Fc:FcγR interaction in a vastly more comprehensive manner than previous approaches, which have included alanine scanning point mutagenesis (Shields et al., *J. Biol. Chem.* 276:6591-6604, 2001), screening random mutagenesis libraries of the entire Fc region (Stavenhagen et al., *Cancer Res.* 67:8882-8890, 2007), and in silico prediction and validation of variants (Lazar et al., *Proc. Natl. Acad. Sci. USA* 103:4005-4010, 2006).

The strength of this approach is highlighted in the variants enriched with substitutions at positions 326-328. While many groups have identified substitutions at position 326 that strengthen FcγR binding affinity (Shields et al., *J. Biol. Chem.* 276:6591-6604, 2001; Stavenhagen et al., *Cancer Res.* 67:8882-8890, 2007, Idusogie et al., *J. Immunol.* 166:2571-2575, 2001), there has been no demonstration that substitutions at positions 327 and 328 can also lead to improved variants. In the context of the two best variants from our screen, IYG and IEA, our data show that mutations at positions 327 and 328 are not additive, yet act in a cooperative fashion to improve binding affinity. Such variants would not be found by combining single point mutations identified for improved binding, and are extremely unlikely to be found in screens of random mutagenesis libraries.

Our yeast display system allows for the rapid screening of millions of variants, and for the most part enriches variants with properties that translate to improved binding when secreted from mammalian cells. It is not without artifacts, however, and this is particularly apparent in the clones enriched from the B/C loop libraries. While there is a clear preference for several similar variants from these libraries, our screening assay suggests that these variants as a whole do not substantially improve receptor binding. This may reflect a limit to the degree to which this loop is capable of improving FcγRIIIA binding (i.e. it has reached its near optimized level), or potentially reflect variations in the affinity that these mutations impart in yeast-secreted antibodies (containing yeast N-linked glycoforms) compared to HEK secreted antibodies (containing human glycosylation patterns).

The following materials and methods were used in connection with the work described above.

Loop Saturation Mutagenesis Library Construction:

Libraries were constructed by homologous recombination of a mutated heavy chain constant region insert into the 4m5.3 heavy chain yeast secretion vector template according to previously published methods (Chao et al., *Nat. Protoc.* 1:755-768, 2006). The 4m5.3 heavy chain secretion vector was previously constructed from the pRS316 shuttle vector by insertion of the GAL10 promoter and alpha terminator, signal peptide, and 4m5.3 variable heavy chain domain upstream of the hIgG$_1$ CH1 to CH3 constant domains (Rakestraw, A directed evolution approach to engineering recombinant protein production in *S. cerevisiae*. Ph.D. thesis (*Massachusetts Institute of Technology*), 2006). The 4m5.3 heavy chain template vector was prepared by digestion with NheI (New England Biolabs) and XhoI (New England Biolabs), which flank the hIgG$_1$ constant domains.

Saturation mutagenesis of the lower hinge was performed by gene reconstruction with the degenerate oligonucleotides 234-237NNK (all oligos from Integrated DNA Technologies) and 236-239NNK; the B/C loop with 265-268NNK and 267-270NNK; and the F/G loop with 326-329NNK, 327-330NNK, 329-332NNK, and 331-334NNK (see the oligonucleotides listed below for sequences of all oligonucleotides used during library construction). Degenerate oligos were designed as 52-mers, with 20 bases of the wild type sequence flanking NNK codons (N=ATCG, K=GT) on both sides. Briefly, in a first PCR step a template for incorporation of the degenerate oligo was created by PCR amplifying the region directly 3' of the desired loop insertion site through the 3' region of the CH3 domain, using the wild type vector as a template. For a given library, this step used the forward primer ###-###flank-for (e.g. 265-268flank-for) and the reverse primer 4m-CH3-epPCR-rev; ###-###flank-for is a 20-mer consisting of the same 3' wild-type sequence in the degenerate oligo, which allows for incorporation of the degenerate oligo in a second PCR step. In this second step, the gel purified PCR product from step one was used as a template for the PCR incorporation and amplification of the degenerate sequence, using the forward primer ###-###NNK (e.g. 265-268NNK) and the reverse primer 4m-CH3-epPCR-rev.

Gene assembly was performed by PCR extension of the above, gel purified PCR product with a second PCR product, consisting of the 5' region of the gene with 20 bp of overlap with the 5' wild-type sequence of the degenerate oligo. This PCR product was amplified from the wild-type vector using the forward primer 4m-CH1-epPCR-for and the reverse oligo ###-###flank-rev (e.g. 265-268flank-rev); ###-###flank-rev is a 20-mer consisting of the same 5' wild-type sequence in the degenerate oligo, allowing for extension of the two PCR products to re-construct the entire CH1-CH3 regions. In a final step, the gel purified extended PCR product was amplified with the oligos 4m-CH1-epPCR-for and 4m-CH3-epPCR-rev, which amplify the 3' region of the 4m5.3 variable heavy chain to the 3' end of the CH3 domain, reconstructing the heavy chain CH1 to CH3 gene insert with ~50 base pairs of overlap with the digested template vector for efficient yeast homologous recombination.

Gene inserts were then transformed with digested template vector by electroporation into the yeast strain YVH10/LC, a derivative of the yeast strain YVH10 (Robinson et al., *Biotechnology* (NY) 12:381-384, 1994), containing a chromosomally integrated copy of the 4m5.3 light chain yeast secretion vector. All saturation libraries had between 1–2×10$^7$ transformants, 10- to 20-fold greater than the theoretical diversity at the DNA level (32$^4$~1.0×10$^6$).

Oligonucleotides:

```
4m-CH1-epPCR-for:
                                    (SEQ ID NO: 12)
(5'-ATGGAATACTTGGGTCAAGGAACCTCAGTCACCGTCTCCGCTAG
C)

4m-CH3-epPCR-rev:
                                    (SEQ ID NO: 13)
(5'-ATTTTGTTACATCTACACTGTTGTTATCAGATTTCGCTCGAGTC
A)

234-237NNK:
                                    (SEQ ID NO: 14)
(5'-CACCGTGCCCAGCACCTGAANNKNNKNNKNNKCCGTCAGTCTTC
CTCTTCCC)

236-239NNK:
                                    (SEQ ID NO: 15)
(5'-GCCCAGCACCTGAACTCCTGNNKNNKNNKNNKGTCTTCCTCTTC
CCCCCAAA)

234-237flank-for:
                                    (SEQ ID NO: 16)
(5'-CCGTCAGTCTTCCTCTTCCC)
```

234-237flank-rev:
(SEQ ID NO: 17)
(5'-TTCAGGTGCTGGGCACGGTG)

236-239flank-for:
(SEQ ID NO: 19)
(5'-GTCTTCCTCTTCCCCCCAAA)

236-239flank-rev:
(SEQ ID NO: 18)
(5'-CATGCGTGGTGGTGGACGTGNNKNNKNNKNNKCCTGAGG
TGAGGTCAAGTT)

265-268NNK:
(SEQ ID NO: 20)
(5'-AGGTCACATGCGTGGTGGTGNNKNNKNNKNNKGAAGACCCTGAG
GTCAAGTT)

267-270NNK:
(SEQ ID NO: 21)
(5'-CATGCGTGGTGGTGGACGTGNNKNNKNNKNNKCCTGAGGTCAAG
TTCAACTG)

265-268flank-for:
(SEQ ID NO: 22)
(5'-GAAGACCCTGAGGTCAAGTT)

265-268flank-rev:
(SEQ ID NO: 23)
(5'-CACCACCACGCATGTGACCT)

267-270flank-for:
(SEQ ID NO: 24)
(5'-CCTGAGGTCAAGTTCAACTG)

267-270flank-rev:
(SEQ ID NO: 25)
(5'-CACGTCCACCACCACGCATG)

326-329NNK:
(SEQ ID NO: 26)
(5'-ACAAGTGCAAGGTCTCCAACNNKNNKNNKNNKGCCCCCATCGAG
AAAACCAT)

327-330NNK:
(SEQ ID NO: 27)
(5'-AGTGCAAGGTCTCCAACAAANNKNNKNNKNNKCCCATCGAGAAA
ACCATCTC)

329-332NNK:
(SEQ ID NO: 28)
(5'-AGGTCTCCAACAAAGCCCTCNNKNNKNNKNNKGAGAAAACCATC
TCCAAAGC)

331-334NNK:
(SEQ ID NO: 29)
(5'-CCAACAAAGCCCTCCCAGCCNNKNNKNNKNNKACCATCTCCAAA
GCCAAAGG)

326-329flank-for:
(SEQ ID NO: 30)
(5'-GCCCCCATCGAGAAAACCAT)

326-329flank-rev:
(SEQ ID NO: 31)
(5'-GTTGGAGACCTTGCACTTGT)

327-330flank-for:
(SEQ ID NO: 32)
(5'-CCCATCGAGAAAACCATCTC)

327-330flank-rev:
(SEQ ID NO: 33)
(5'-TTTGTTGGAGACCTTGCACT)

329-332flank-for:
(SEQ ID NO: 34)
(5'-GAGAAAACCATCTCCAAAGC)

329-332flank-rev:
(SEQ ID NO: 35)
(5'-GAGGGCTTTGTTGGAGACCT)

331-334flank-for:
(SEQ ID NO: 36)
(5'-ACCATCTCCAAAGCCAAAGG)

331-334flank-rev:
(SEQ ID NO: 37)
(5'-GGCTGGGAGGGCTTTGTTGG)

Library Screening:

Library screening was performed using the cell surface secretion assay (CeSSA) (Rakestraw et al., *Biotechnol. Prog.* 22, 22:1200-1208, 2006). Briefly, pooled loop libraries were grown in SD-CAA (2% glucose, 0.67% yeast nitrogen base, 0.54% $Na_2HPO_4$, 0.86% $NaH_2PO_4.H_2O$, 0.5% casein amino acids) to an $OD_{600}$ of ~5, and then induced in YPG (2% galactose, 2% peptone, 1% yeast extract, 0.54% $Na_2HPO_4$, 0.86% $NaH_2PO_4.H_2O$) for 12 hrs at 20° C. Following this pre-induction phase, yeast were labeled with fluorescein-PEG-NHS (Nektar) and re-induced in YPG containing 15% PEG (w/v) at 20° C. for 36 hrs. Cells were then washed with PBS containing 0.1% (w/v) BSA (PBS/BSA).

For the first two rounds of screening, libraries were incubated with biotinylated hFcγRIIIA[176F] preloaded onto streptavidin magnetic beads (Invitrogen), and enriched variants captured by magnetic separation, with non-bound yeast discarded. Beads were washed with PBS/BSA, then placed in SD-CAA supplemented with penicillin/streptomycin (Invitrogen) to amplify captured yeast cells. Starting with the third round of screening, yeast were labeled with biotinylated hFcγRIIIA[176F] preloaded onto streptavidin-Alexa 647 (Invitrogen). The subpopulations were sorted on either a BD FACSAria (Becton Dickinson) or a MoFlo Cell Sorter (Cytomation Inc) and collected cells grown in SD-CAA supplemented with penicillin/streptomycin (Invitrogen), for three additional rounds of screening (five rounds in total). Library populations were labeled for FACS sorting at increasingly stringent concentrations of FcγRIIIA[176F] tetramer as follows: round three (500 pM), round four (50 pM), and round five (50 pM).

Cloning and Site Directed Mutagenesis:

Clones enriched from the yeast-based screen were cloned from the yeast secretion vectors into the gWIZ mammalian expression vector (Genlantis) by a variation of the Quikchange mutagenesis protocol (Geiser et al., *Biotechniques;* 31:88-90, 2001). Fc domains were PCR amplified from the pRS316 based heavy chain yeast secretion vector with the oligos:

gWIZ-Fc-for =
(SEQ ID NO: 38)
(5'-GAGCCCAAATCTTGTGACAA)

gWIZ-SalI-rev =
(SEQ ID NO: 39)
(5'-TCACACGTGTCGACTTATCATTTACCCGGAGACAGGGAGA)

These primers allow for ≥20 bp of homology to the wild-type segment in the gWIZ vector. PCR products were gel purified and used as oligos for PCR-amplification of the entire variant vector, incorporating the sequence of the Fc variant.

Point mutants were constructed by PCR-amplification of the entire vector using complementary primers containing the desired point mutations.

Characterization of HEK-Secreted Fc Mutants:

Unless otherwise noted, Fc variants were transiently transfected into HEK 293F cells (Invitrogen) in a 6-well plate format. Cell culture supernatants were loaded onto fluorescein-conjugated yeast overnight at 4° C.; yeast were then washed with PBS/BSA, labeled with biotinylated FcγR preloaded onto streptavidin-Alexa 647 at 4° C. for >2 hrs, and analyzed by flow cytometry. Labeling with 10 µg/ml Protein A-Alexa 647 (Invitrogen) was performed as a separate IgG loading control for all samples. FcγR labeling fluorescence for individual variants was normalized by the surface IgG loading of a variant relative to that of wild-type IgG, as determined by relative Protein A-Alexa 647 labeling. There was strong agreement (within 10% difference) between this approach to signal normalization and gating on a population of cells to give similar surface loading signals.

Antibodies and Recombinant Proteins:

The 4m5.3-human Fc chimeric variants were produced by transient transfection of 293F cells (Invitrogen) and subsequent purification from cell culture supernatants. For protein production, cells were cultured in Freestyle 293F Expression Medium (Invitrogen). Recombinant antibodies were purified with immobilized protein A (Pierce) by affinity chromatography. All proteins were dialyzed against PBS. Purity was assessed by SDS-PAGE followed by Coomassie Blue staining.

A number of embodiments of the invention have been described. Nevertheless, it will be understood that various modifications may be made without departing from the spirit and scope of the invention. Accordingly, other embodiments are within the scope of the following claims.

What is claimed is:

1. An IgG antibody comprising a first mutation in the C'/E loop of the CH2 domain of the Fc region that eliminates antibody glycosylation in the CH2 domain and a second mutation in the F/G loop of the CH2 domain, wherein the antibody exhibits at least 50% binding activity to activating receptor FcγRIIA or FcγRIIIA, relative to the corresponding wild type antibody, wherein the mutation in the F/G loop of the CH2 domain comprises K326I.

2. The antibody of claim 1, comprising the mutations (a) K326I, (b) A327Y or A327E, and (c) L328G or L328A.

3. The antibody of claim 1, wherein the antibody specifically binds a cancer antigen or is useful as a cancer therapeutic.

4. The antibody of claim 1, wherein the mutation in the F/G loop of the CH2 domain comprises K326I, A327Y, and L328G.

5. The antibody of claim 1, wherein the mutation in the F/G loop of the CH2 domain comprises K326I, A327E, and L328A.

6. The antibody of claim 1, wherein the mutation in the C'/E loop of the CH2 domain comprises N297H and S298A; T299A; N297D and S298T; or N297D and S298A.

7. The antibody of claim 4, wherein the mutation in the C'/E loop of the CH2 domain comprises N297H and S298A; T299A; N297D and S298T; or N297D and S298A.

8. The antibody of claim 5, wherein the mutation in the C'/E loop of the CH2 domain comprises N297H and S298A; T299A; N297D and S298T; or N297D and S298A.

9. The antibody of claim 1, wherein first mutation in the C'/E loop of the CH2 domain comprises N297H, S298A, T299A, N297D, S298G, or S298T.

10. The antibody of claim 1, wherein the first mutation in the C'/E loop comprises a mutation at position 298 and/or 299 of the CH2 domain.

11. The antibody of claim 1, comprising one or more of the following mutations: E269D, D270E, N297D, N297H, S298A, S298G, S298T, T299A, T299G, T299H, K326E, K326I, A327E, A327Y, L328A, and L328G.

12. A pharmaceutically acceptable composition comprising the antibody of claim 1.

13. A nucleic acid comprising a sequence encoding the antibody of claim 1.

14. An expression vector comprising the nucleic acid of claim 13.

15. The expression vector of claim 14, further comprising a leader sequence.

16. A host cell comprising the expression vector of claim 14.

17. An IgG antibody comprising a first mutation in the C'/E loop of the CH2 domain of the Fc region that eliminates antibody glycosylation in the CH2 domain and a second mutation in the F/G loop of the CH2 domain, wherein the antibody exhibits at least 50% binding activity to activating receptor FcγRIIA or FcγRIIIA, relative to the corresponding wild type antibody, wherein the mutation in the C'/E loop of the CH2 domain comprises N297H and S298A; T299A; N297D and S298T; or N297D and S298A, and further wherein the mutation in the F/G loop of the CH2 domain comprises K326I, A327Y, and L328G; or K326I, A327E, and L328A.

18. The IgG antibody of claim 17, wherein the antibody specifically binds a cancer antigen.

19. The IgG antibody of claim 17, wherein the cancer antigen is selected from carcinoembryonic antigen (CEA), RAGE, MART (melanoma antigen), MAGE (melanoma antigen) 1-4, 6 and 12; MUC (mucin)-1 or 2, tyrosinase, Pmel 17 (gp100), GnT-V intron V sequence (N-acetylglucoaminyl-transferase V intron V sequence), Prostate cancer psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP) Bcl-2, prostate specific antigen (PSA), and Ki-67.

\* \* \* \* \*

```
                          SEQUENCE LISTING

<160> NUMBER OF SEQ ID NOS: 129

<210> SEQ ID NO 1
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28
<223> OTHER INFORMATION: n = A,T,C or G
<220> FEATURE:
<221> NAME/KEY: misc_feature
<222> LOCATION: 21, 22, 24, 25, 27, 28
<223> OTHER INFORMATION: n = A,T,C or G

<400> SEQUENCE: 1
agccgcggga ggagcagtac nnknnknnkt accgtgtggt cagcgtcct            49

<210> SEQ ID NO 2
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 2
caaagccgcg ggaggagcag nnknnknnkn nktaccgtgt ggtcagcgtc ct         52

<210> SEQ ID NO 3
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G
```

-continued

<400> SEQUENCE: 3
agccgcggga ggagcagtac nnknnknnkn nkcgtgtggt cagcgtcctc ac    52

<210> SEQ ID NO 4
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 4
atggaatact tgggtcaagg aacctcagtc accgtctccg ctagc    45

<210> SEQ ID NO 5
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 5
attttgttac atctacactg ttgttatcag atttcgctcg agtca    45

<210> SEQ ID NO 6
<211> LENGTH: 41
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 19, 20
<223> OTHER INFORMATION: n = A,T,C or G
<220> FEATURE:
<221> NAME/KEY: misc_feature
<222> LOCATION: 19, 20
<223> OTHER INFORMATION: n = A,T,C or G

<400> SEQUENCE: 6
ccgcgggagg agcagtacnn kagcacgtac cgtgtggtca g    41

<210> SEQ ID NO 7
<211> LENGTH: 41
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 20, 21
<223> OTHER INFORMATION: n = A,T,C or G
<220> FEATURE:
<221> NAME/KEY: misc_feature
<222> LOCATION: 20, 21
<223> OTHER INFORMATION: n = A,T,C or G

<400> SEQUENCE: 7
gcgggaggag cagtacaacn nkacgtaccg tgtggtcagc g    41

<210> SEQ ID NO 8
<211> LENGTH: 40
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 20, 21
<223> OTHER INFORMATION: n = A,T,C or G

```
<220> FEATURE:
<221> NAME/KEY: misc_feature
<222> LOCATION: 20, 21
<223> OTHER INFORMATION: n = A,T,C or G

<400> SEQUENCE: 8
ggaggagcag tacaacagcn nktaccgtgt ggtcagcgtc                                40

<210> SEQ ID NO 9
<211> LENGTH: 41
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 19
<223> OTHER INFORMATION: n = A,T,C or G
<220> FEATURE:
<221> NAME/KEY: misc_feature
<222> LOCATION: 19
<223> OTHER INFORMATION: n = A,T,C or G

<400> SEQUENCE: 9
ccgcgggagg agcagtacnh cagcacgtac cgtgtggtca g                             41

<210> SEQ ID NO 10
<211> LENGTH: 41
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 20
<223> OTHER INFORMATION: n = A,T,C or G
<220> FEATURE:
<221> NAME/KEY: misc_feature
<222> LOCATION: 20
<223> OTHER INFORMATION: n = A,T,C or G

<400> SEQUENCE: 10
gcgggaggag cagtacaacn hcacgtaccg tgtggtcagc g                             41

<210> SEQ ID NO 11
<211> LENGTH: 40
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 20
<223> OTHER INFORMATION: n = A,T,C or G
<220> FEATURE:
<221> NAME/KEY: misc_feature
<222> LOCATION: 20
<223> OTHER INFORMATION: n = A,T,C or G

<400> SEQUENCE: 11
ggaggagcag tacaacagcn hctaccgtgt ggtcagcgtc                               40

<210> SEQ ID NO 12
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 12
```
atggaatact tgggtcaagg aacctcagtc accgtctccg ctagc                              45

<210> SEQ ID NO 13
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 13
attttgttac atctacactg ttgttatcag atttcgctcg agtca                              45

<210> SEQ ID NO 14
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 14
caccgtgccc agcacctgaa nnknnknnkn nkccgtcagt cttcctcttc cc                      52

<210> SEQ ID NO 15
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 15
gcccagcacc tgaactcctg nnknnknnkn nkgtcttcct cttcccccca aa                      52

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
ccgtcagtct tcctcttccc                                                          20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
ttcaggtgct gggcacggtg                                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
caggagttca ggtgctgggc                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
gtcttcctct tcccccaaa                                               20

<210> SEQ ID NO 20
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 20
aggtcacatg cgtggtggtg nnknnknnkn nkgaagaccc tgaggtcaag tt           52

<210> SEQ ID NO 21
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 21
catgcgtggt ggtggacgtg nnknnknnkn nkcctgaggt caagttcaac tg           52

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
gaagaccctg aggtcaagtt                                              20

<210> SEQ ID NO 23
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 23
caccaccacg catgtgacct                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
cctgaggtca agttcaactg                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
cacgtccacc accacgcatg                                               20

<210> SEQ ID NO 26
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 26
acaagtgcaa ggtctccaac nnknnknnkn nkgcccccat cgagaaaacc at           52

<210> SEQ ID NO 27
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 27
agtgcaaggt ctccaacaaa nnknnknnkn nkcccatcga gaaaaccatc tc           52

<210> SEQ ID NO 28
<211> LENGTH: 52
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 28
aggtctccaa caaagccctc nnknnknnkn nkgagaaaac catctccaaa gc        52

<210> SEQ ID NO 29
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 21, 22, 24, 25, 27, 28, 30, 31
<223> OTHER INFORMATION: n = A,T,C or G
<220> FEATURE:
<221> NAME/KEY: misc_feature
<222> LOCATION: 21, 22, 24, 25, 27, 28, 30, 31
<223> OTHER INFORMATION: n = A,T,C or G

<400> SEQUENCE: 29
ccaacaaagc cctcccagcc nnknnknnkn nkaccatctc caaagccaaa gg        52

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
gcccccatcg agaaaaccat                                             20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
gttggagacc ttgcacttgt                                             20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
cccatcgaga aaaccatctc                                             20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
```
tttgttggag accttgcact                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
gagaaaacca tctccaaagc                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
gagggctttg ttggagacct                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
accatctcca aagccaaagg                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
ggctgggagg gctttgttgg                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
gagcccaaat cttgtgacaa                                              20

<210> SEQ ID NO 39
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 39
tcacacgtgt cgacttatca tttacccgga gacagggaga                        40

<210> SEQ ID NO 40
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 40

Tyr Asn Ser Thr Tyr
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 41

Tyr Asn Gly Gly Tyr
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 42

Tyr Asn Gly Gly Lys
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 43

Tyr Asn Gly Gly Asp
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 44

Tyr Asn Gly Gly Gln
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 45

Tyr Asn Gly Gly Trp
1               5

<210> SEQ ID NO 46
<211> LENGTH: 5
<212> TYPE: PRT
<213> ORGANISM: Artificial Sequence
<220> FEATURE:

```
<223> OTHER INFORMATION: Synthetic Polypeptide

<400> SEQUENCE: 46

Asp Asn Gly Ala Tyr
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 47

Tyr Asn Gly Ala Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 48

Tyr Asn Gly Ala Cys
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 49

Tyr Asn Gly Ala Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 50

Tyr Asn Ser Ala Tyr
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 51

Tyr Asn Gly Ala Tyr
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 52

Tyr Asn Gly Ala Asp
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 53

Tyr Asn Gly Ala Gly
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 54

Tyr Asn Gly Ala Val
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 55

Tyr Asn Gly Ala Thr
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 56

Tyr Asn Gly Ala Ile
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 57

Tyr Asn Gly Ala Trp
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 58

Tyr Asn Gly Ala Glu
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 59

Tyr Asn Gly Gly Ile
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 60

Tyr Asn Ser Ala Tyr
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 61

Ala Phe Lys Phe Phe His Trp
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 62

Ser Gln Lys Phe Ser Arg Leu
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 63

Ser Gln Lys Phe Ser His Leu
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 64
```

```
Ser Lys Lys Phe Ser Arg Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 65

Asp Arg Lys Tyr Phe His His
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 66

Leu Leu Gly Gly Pro Ser
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 67

Asp Val Ser His Glu Asp
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 68

Lys Ala Leu Pro Ala Pro Ile Glu Lys
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 69

Asp Leu Glu Glu Glu Asp
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 70
```

Asp Leu Ala Glu Glu Asp
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 71

Asp Leu Ser Gln Glu Asp
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 72

Asp Val Ala Glu Asp Asp
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 73

Asp Val Ala Glu Glu Asp
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 74

Asp Val Ala Glu Glu Glu
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 75

Asp Val Ser Glu Asp Asp
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 76

Asp Val Ser Glu Glu Asp

```
1               5
```

<210> SEQ ID NO 77
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 77

```
Asp Val Asp Asp Glu Asp
1               5
```

<210> SEQ ID NO 78
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 78

```
Asp Val Asp Asp Glu Glu
1               5
```

<210> SEQ ID NO 79
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 79

```
Asp Val Gln Asp Asp Asp
1               5
```

<210> SEQ ID NO 80
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 80

```
Asp Val Ser Asp Asp Asp
1               5
```

<210> SEQ ID NO 81
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 81

```
Asp Val Ser Thr Glu Glu
1               5
```

<210> SEQ ID NO 82
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 82

```
Asp Leu Glu Glu Glu Asp
1               5
```

```
<210> SEQ ID NO 83
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 83

Asp Leu Ala Glu Glu Asp
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 84

Asp Leu Thr Glu Glu Asp
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 85

Asp Leu Ser Glu Glu Asp
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 86

Asp Val Ala Glu Asp Asp
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 87

Ile Ala Gly Pro Ala Pro Ile Glu Lys
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 88

Ile Tyr Gly Pro Ala Pro Ile Glu Lys
1               5
```

```
<210> SEQ ID NO 89
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 89

Ile Asp Ala Pro Ala Pro Ile Glu Lys
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 90

Lys Gly Ala Pro Ala Pro Ile Glu Lys
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 91

Lys Ala Leu Ala Glu Pro Glu Glu Lys
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 92

Lys Ala Leu Ala Tyr Pro Glu Glu Lys
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 93

Lys Ala Leu Pro Val Pro Glu Glu Lys
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 94

Lys Ala Leu Pro Ser Ala Glu Glu Lys
1               5
```

```
<210> SEQ ID NO 95
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 95

Lys Ala Leu Pro Ala Ala Ile Ser Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 96

Lys Ala Leu Pro Ala Ser Ile Gln Ala
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 97

Lys Ala Leu Pro Ala Ser Glu Glu Ala
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 98

Lys Ala Leu Pro Ala Ser Glu Glu Val
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 99

Lys Ala Leu Pro Ala Pro Glu Glu Val
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 100

Lys Ala Leu Pro Ala Pro Thr Glu Val
1               5

<210> SEQ ID NO 101
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 101

Lys Ala Leu Pro Ala Pro Gln Glu Val
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 102

Lys Ala Leu Pro Ala Pro Val Gln Glu
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 103

Val Asp Ala Pro Ala Pro Ile Glu Lys
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 104

Leu Asp Ala Pro Ala Pro Ile Glu Lys
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 105

Ile Asp Ala Pro Ala Pro Ile Glu Lys
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 106

Ile Glu Ala Pro Ala Pro Ile Glu Lys
1               5

<210> SEQ ID NO 107
<211> LENGTH: 9
```

```
<212> TYPE: PRT
<213> ORGANISM: Artificial Sequence
<220> FEATURE:
<223> OTHER INFORMATION: Synthetic Polypeptide

<400> SEQUENCE: 107

Ile Ala Ala Pro Ala Pro Ile Glu Lys
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 108

Leu Ala Ala Pro Ala Pro Ile Glu Lys
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 109

Ile Asp Thr Pro Ala Pro Ile Glu Lys
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 110

Glu Gly Ala Pro Ala Pro Ile Glu Lys
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 111

Asp Ala Val Pro Ala Pro Ile Glu Lys
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 112

Lys Ala Leu Val Met Pro Glu Glu Lys
1               5

<210> SEQ ID NO 113
<211> LENGTH: 9
<212> TYPE: PRT
```

```
<213> ORGANISM: Artificial Sequence
<220> FEATURE:
<223> OTHER INFORMATION: Synthetic Polypeptide

<400> SEQUENCE: 113

Lys Ala Leu Pro Met Pro Glu Glu Lys
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 114

Lys Ala Leu Pro Leu Pro Glu Glu Lys
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 115

Lys Ala Leu Pro Gln Pro Glu Glu Lys
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 116

Lys Ala Leu Pro Tyr Pro Glu Glu Lys
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 117

Lys Ala Leu Pro Ala Ala Glu Val Glu
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 118

Lys Ala Leu Pro Ala Ala Glu Ser Val
1               5

<210> SEQ ID NO 119
<211> LENGTH: 9
<212> TYPE: PRT
<213> ORGANISM: Artificial Sequence
```

```
<220> FEATURE:
<223> OTHER INFORMATION: Synthetic Polypeptide

<400> SEQUENCE: 119

Lys Ala Leu Pro Ala Ala Glu Glu Val
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 120

Lys Ala Leu Pro Ala Ala Glu Glu Gln
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 121

Lys Ala Leu Pro Ala Ser Glu Val Ala
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 122

Lys Ala Leu Pro Ala Ser Glu Glu Val
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 123

Lys Ala Leu Pro Ala Pro Glu Glu Lys
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 124

Lys Ala Leu Pro Ala Pro Glu Glu Ala
1               5

<210> SEQ ID NO 125
<211> LENGTH: 9
<212> TYPE: PRT
<213> ORGANISM: Artificial Sequence
<220> FEATURE:
```

```
<223> OTHER INFORMATION: Synthetic Polypeptide

<400> SEQUENCE: 125

Lys Ala Leu Pro Ala Pro Glu Ser Ala
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 126

Lys Ala Leu Pro Ala Pro Glu Ile Ala
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 127

Lys Ala Leu Pro Ala Pro Glu Glu Val
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 128

Lys Ala Leu Pro Ala Pro Glu Tyr Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 129

Lys Ala Leu Pro Ala Pro Ile His Glu
1               5
```